(12) United States Patent
Sadakane et al.

(10) Patent No.: US 8,254,520 B2
(45) Date of Patent: Aug. 28, 2012

(54) IMAGE PROCESSING METHOD, IMAGE DISPLAY METHOD, IMAGE PROCESSING PROGRAM, STORAGE MEDIUM, IMAGE PROCESSING APPARATUS AND X-RAY IMAGING APPARATUS

(75) Inventors: Tomoyuki Sadakane, Kyoto (JP); Masakazu Suzuki, Kyoto (JP); Hideki Yoshikawa, Kyoto (JP); Teruji Nakai, Kyoto (JP); Tetsuzo Ito, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 68 days.

(21) Appl. No.: 12/069,067

(22) Filed: Feb. 7, 2008

(65) Prior Publication Data

US 2009/0052617 A1    Feb. 26, 2009

(30) Foreign Application Priority Data

Feb. 22, 2007  (JP) ................................ 2007-042139
Jan. 25, 2008  (JP) ................................ 2008-014799

(51) Int. Cl.
*A61B 6/14* (2006.01)
(52) U.S. Cl. .......................................... 378/38; 378/19
(58) Field of Classification Search .............. 378/38–39, 378/19
See application file for complete search history.

(56) References Cited

U.S. PATENT DOCUMENTS

| | | | | |
|---|---|---|---|---|
| 6,493,415 B1 * | 12/2002 | Arai et al. | ........................... | 378/4 |
| 2004/0066877 A1 * | 4/2004 | Arai et al. | ........................... | 378/4 |
| 2005/0117696 A1 * | 6/2005 | Suzuki et al. | ..................... | 378/19 |
| 2006/0239400 A1 * | 10/2006 | Sukovic et al. | .................. | 378/38 |
| 2006/0275740 A1 * | 12/2006 | Singh et al. | ..................... | 433/215 |
| 2008/0232539 A1 * | 9/2008 | Pasini et al. | ....................... | 378/4 |

FOREIGN PATENT DOCUMENTS

| | | |
|---|---|---|
| DE | 100 08 053 A | 9/2001 |
| DE | 100 47 993 A | 4/2002 |
| JP | 08-215192 | 8/1996 |
| JP | H08-215192 A | 8/1996 |
| JP | 2000-057789 | 2/2000 |
| JP | 2001-61834 | 3/2001 |
| JP | 2002-153458 A | 5/2002 |
| JP | 2003-290220 A | 10/2003 |
| JP | 2005-13363 A | 2/2005 |
| WO | WO 02/28285 A | 4/2002 |
| WO | WO 2006/033483 A | 3/2006 |

OTHER PUBLICATIONS

Synthesizing panoramic radiographs by unwrapping dental CT data by Sirilawan Tohnak et al. in Proceeding of the 28th IEEE Annual International Conference, p. 3329-3332, in 2006.

* cited by examiner

*Primary Examiner* — Hoon Song
(74) *Attorney, Agent, or Firm* — DLA Piper LLP (US)

(57) ABSTRACT

An object of the present invention is to provide an image processing method, etc. capable of producing a panorama tomogram with a simple operation whenever required by the operator. The present invention relates to an image processing method for producing a panorama tomogram of the dental arch using the X-ray projection data on the dentomaxillofacial region obtained by the X-ray computer tomography. The image processing method according to the present invention includes the steps of retrieving the dental arch projection data corresponding to the dental arch from the X-ray projection data based on the preset position and shape information to specify the position and shape of the dental arch from the X-ray projection data (S3) and generating a panorama tomogram by executing a predetermined process using the dental arch projection data (S4).

23 Claims, 17 Drawing Sheets

69

FIG. 22
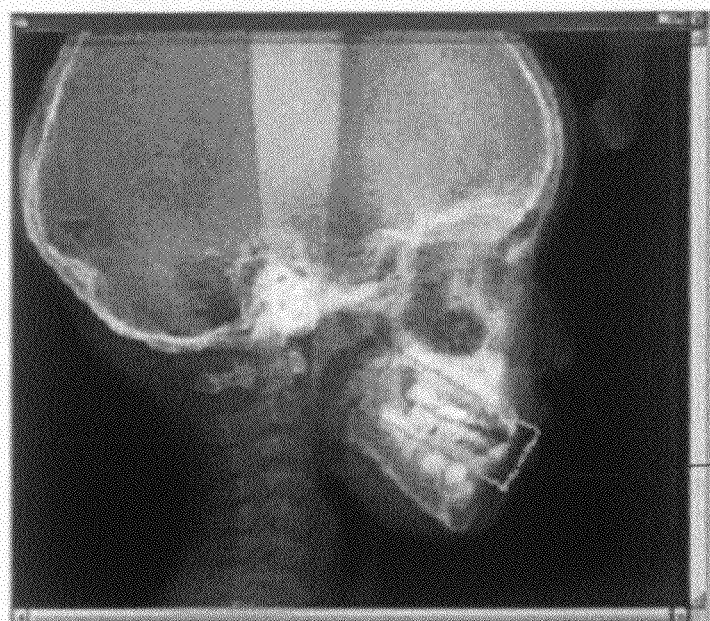
81
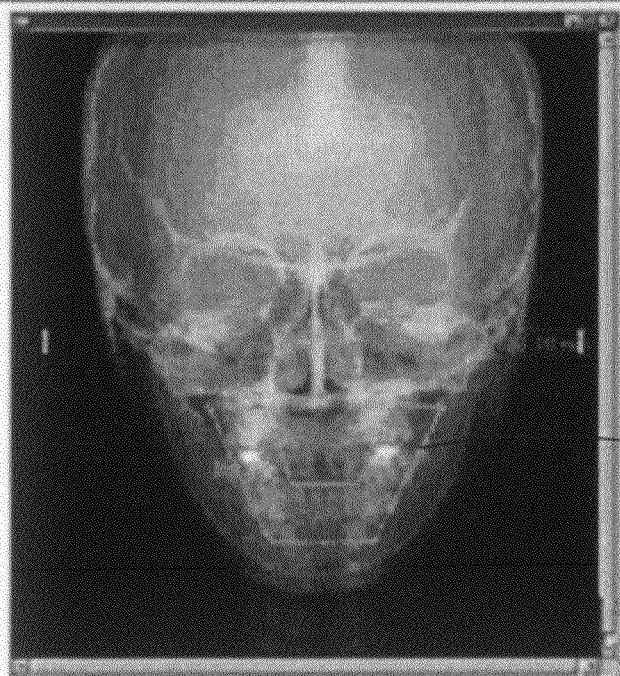
81

FIG. 23
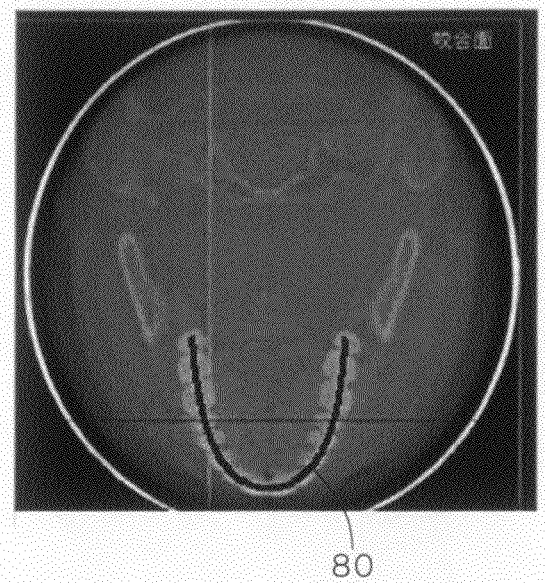
FIG. 24
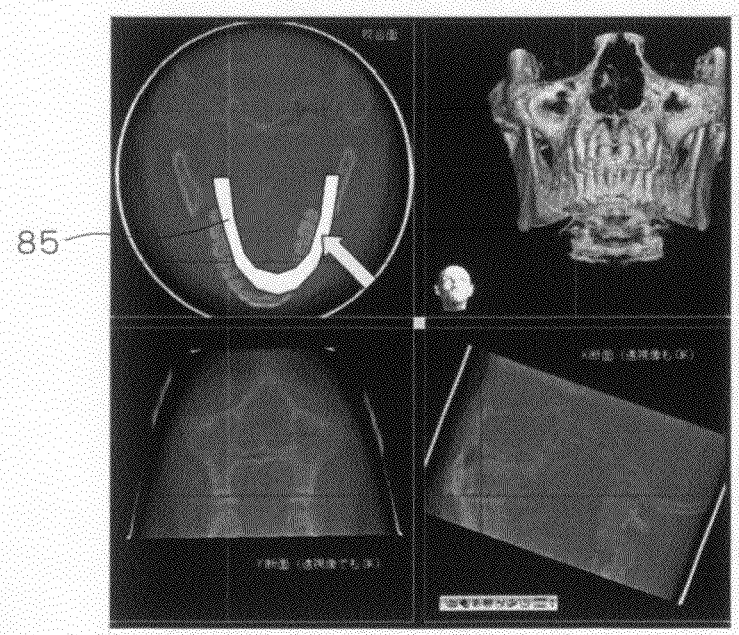
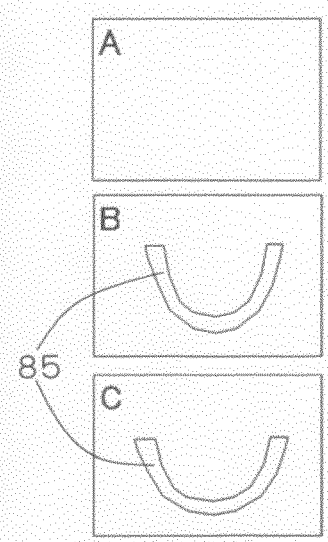

IMAGE PROCESSING METHOD, IMAGE DISPLAY METHOD, IMAGE PROCESSING PROGRAM, STORAGE MEDIUM, IMAGE PROCESSING APPARATUS AND X-RAY IMAGING APPARATUS

BACKGROUND OF THE INVENTION

1. Field of the Invention

The present invention relates to an image processing method, etc., or in particular, to an image processing method, etc. for X-ray computer tomography.

2. Description of the Background Art

Conventionally, the panorama X-ray imaging apparatus for tomography along the dental arch is known in the field of dental diagnosis. In this panorama X-ray imaging apparatus, an X-ray source and an X-ray imaging means arranged in opposed relation to the X-ray source are moved along a predetermined trajectory with the head of an object located therebetween, thereby producing a panorama tomogram along the dental arch.

Also, in the field of dental diagnosis, the X-ray CT (computer tomography method) for tomographically imaging an arbitrary part of the human body is used. In this X-ray computer tomography apparatus, the X-ray source and the X-ray imaging means arranged in opposed relation to the X-ray source are rotated in a predetermined direction with the head of an object held therebetween, and the resulting image signal is processed by the computer. In this way, the X-ray projection data is reconstructed, so that a sectional image of an arbitrary part of the head, etc. cut at an arbitrary angle or a three-dimensional volume data can be obtained.

A method of producing a panorama tomogram from the X-ray projection data on the dentomaxillofacial region obtained from the X-ray computer tomography apparatus is disclosed in Japanese Patent Application Laid-Open No. 08-215192, Japanese Patent Application Laid-Open No. 2001-061834 and Japanese Patent Application Laid-Open No. 2000-057789. Specifically, Japanese Patent Application Laid-Open No. 08-215192 discloses a technique in which a plurality of coordinate points are input from the sliced images of the occlusal surface obtained by the X-ray computer tomography apparatus thereby to designate the panorama curve of the dental arch, so that the panorama image of the dental arch is displayed on the one hand and an oblique image (an arbitrary sectional view or an inclined sectional view) of the region of interest is displayed by designating the oblique line on the other hand.

Also, Japanese Patent Application Laid-Open No. 2001-061834 discloses a technique in which a reference curved surface and a curved thick plate region are designated from the three-dimensional volume data constituting the X-ray projection data subjected to CT reconstruction thereby to produce a panorama tomogram of the dental arch. Further, Japanese Patent Application Laid-Open No. 2000-057789 discloses a technique in which the three-dimensional distribution information on the projection line in the direction crossing the panorama layer plane at a predetermined angle is calculated based on the projection data obtained by the X-ray computer tomography, and the calculation result is developed on the two-dimensional plane thereby to generate a panorama tomogram.

In Japanese Patent Application Laid-Open No. 08-215192, Japanese Patent Application Laid-Open No. 2001-061834 and Japanese Patent Application Laid-Open No. 2000-057789, there is a common merit to obtain a panorama tomogram based on the X-ray projection data imaged by the X-ray computer tomography apparatus. That is the merit that by once obtaining the X-ray projection data imaged by the X-ray computer tomography apparatus required no image taking for obtaining a panorama tomogram. The merit also has further advantage of not being exposed to unnecessary X-ray. However, in Japanese Patent Application Laid-Open No. 08-215192, a problem involved in immense amount of time and effort has arisen that at the time when displaying the panorama tomogram and the oblique image from the imaged data, a complicated operation such as inputting a plurality of coordinate points and parameters is required. Similarly, in Japanese Patent Application Laid-Open No. 2001-061834 and Japanese Patent Application Laid-Open No. 2000-057789, there has been a problem that in order to obtain the panorama tomogram, it is necessary for an operator to conduct a complicated operation such as setting a reference curve. Otherwise he/she is not allowed to obtain the panorama tomogram with ease.

SUMMARY OF THE INVENTION

An object of the present invention is to provide an image processing method, etc. wherein a panorama tomogram can be obtained by a simple operation based on the X-ray projection data obtained by an X-ray CT tomography apparatus, and without the labor of setting a plurality of coordinate points or setting a reference curve on the part of the operator, a panorama tomogram of the dental arch can be obtained whenever required by the operator without mastering the operation of the apparatus.

According to the present invention, there is provided an image processing method for producing a panorama tomogram of a dentition using the X-ray projection data on the dentomaxillofacial region obtained by the X-ray computer tomography. The image processing method according to the present invention includes the steps of extracting the dental arch projection data corresponding to the dental arch from the X-ray projection data based on the preset position and shape information to specify the position and the shape of the dental arch in the X-ray projection data and generating the panorama tomogram by executing a predetermined process using the dental arch projection data.

In the image processing method according to the present invention, the panorama tomogram can be produced without any operation after X-ray computer tomography or simply by operating a select switch such as "panorama display" or the like only once. Also, the CT image and the panorama tomogram can be displayed based on the X-ray projection data obtained by one session of X-ray computer tomography. Therefore, the X-ray exposure dosage can be suppressed to one session of the head computer tomography. Further, in the image processing method according to the present invention, in a case where the X-ray projection data obtained by X-ray computer tomography is reconstructed into a three-dimensional volume data and a panorama tomogram is generated by extracting the data required for the panorama tomogram from the three-dimensional volume data a plurality of different formats can be displayed using a single data, thereby contributing to the effective data utilization. In a case where the X-ray projection data obtained by X-ray computer tomography is not reconstructed into the three-dimensional volume data but the part of the X-ray projection data required for the panorama tomogram is directly extracted, on the other hand, the processing time can be shortened and substantially the same image as the panorama tomogram obtained by the X-ray panorama imaging operation can be produced due to a lack of a metal artifact.

In the image display method according to the present invention, the panorama tomogram obtained by the image processing method is displayed either before the images other than the panorama tomogram obtained by the X-ray computer tomography or at the same time as at least one image other than the panorama tomogram. In this image processing method, the panorama tomogram of the dentition is produced using the X-ray projection data on the dentomaxillofacial region obtained by the X-ray computer tomography including the steps of extracting the dental arch projection data corresponding to the dental arch from the X-ray projection data based on the preset position and shape information to specify the position and shape of the dental arch in the X-ray projection data and generating the panorama tomogram by executing a predetermined process using the dental arch projection data.

In the image display method according to the present invention, the panorama tomogram is displayed either before the images other than the panorama tomogram obtained by X-ray computer tomography or at the same time as at least one image other than the panorama tomogram. Therefore, the dentist can first confirm the panorama tomogram to which he/she is accustomed and therefore can make efficient diagnosis.

In the image processing program according to the present invention, the processing steps of the image processing method for producing the panorama tomogram of the dentition using the X-ray projection data on the dentomaxillofacial region obtained by the X-ray computer tomography are executed by the computer, the X-ray computer tomography including the steps of extracting the dental arch projection data corresponding to the dental arch from the X-ray projection data based on the preset position and shape information to specify the position and shape of the dental arch in the X-ray projection data and generating a panorama tomogram by executing a predetermined process using the dental arch projection data.

The image processing program according to the present invention can produce the panorama tomogram with a simple operation. Also, by version-up of the existing X-ray computer tomography apparatus or the image processing apparatus using the image processing program, the panorama image producing function can be easily added, and therefore, the panorama imaging apparatus is not specially required.

The image processing apparatus according to the present invention includes a storage means, a dental arch projection data extraction means and a panorama generating means. The storage means stores the X-ray projection data on the dentomaxillofacial region obtained by the X-ray computer tomography. The dental arch projection data extraction means extracts the dental arch projection data corresponding to the dental arch from the X-ray projection data based on the preset position and shape information to specify the position and shape of the dental arch in the X-ray projection data. The panorama generating means generates the panorama tomogram by executing a predetermined process using the dental arch projection data.

In the image processing apparatus according to the present invention, a panorama tomogram can be obtained without any operation after X-ray computer tomography or by a single operation of the select switch such as panorama display or the like.

The X-ray imaging apparatus according to the present invention includes an X-ray source, an X-ray image sensor, a supporting means, a rotary drive means and an image processing means. The X-ray source generates the X-ray. The X-ray image sensor detects the X-ray passed through the object. The supporting means supports the X-ray source and the X-ray image sensor in opposed relation to each other with the head of the object arranged therebetween. The rotary drive means rotates the supporting means at the time of X-ray computer tomography. The image processing means includes a storage means for storing the X-ray projection data on the dentomaxillofacial region obtained by the X-ray computer tomography, a dental arch projection data extraction means for retrieving the dental arch projection data corresponding to the dental arch from the X-ray projection data based on the preset position and shape information to specify the position and shape of the dental arch in the X-ray projection data, and a panorama generating means for generating the panorama tomogram by executing a predetermined process using the dental arch projection data.

The X-ray imaging apparatus according to this invention can produce the panorama tomogram with a simple operation.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 18 to 24 are diagrams describing specific cases of the position specifying steps in the image processing method according to the second embodiment of the present invention.

DESCRIPTION OF THE PREFERRED EMBODIMENTS

First Embodiment
(General Description)

The present invention according to this embodiment relates to an image processing method capable of easily producing a panorama tomogram of the dental arch using the X-ray projection data on the dentomaxillofacial region obtained by the X-ray computer tomography, an image processing apparatus and an X-ray imaging apparatus for executing the method. Also, the present invention according to this embodiment relates to an image processing program for causing the computer to execute the processing steps of the image processing method and a computer-readable recording medium for recording the image processing program.

(Configuration of X-Ray Imaging Apparatus)

Figure 1:
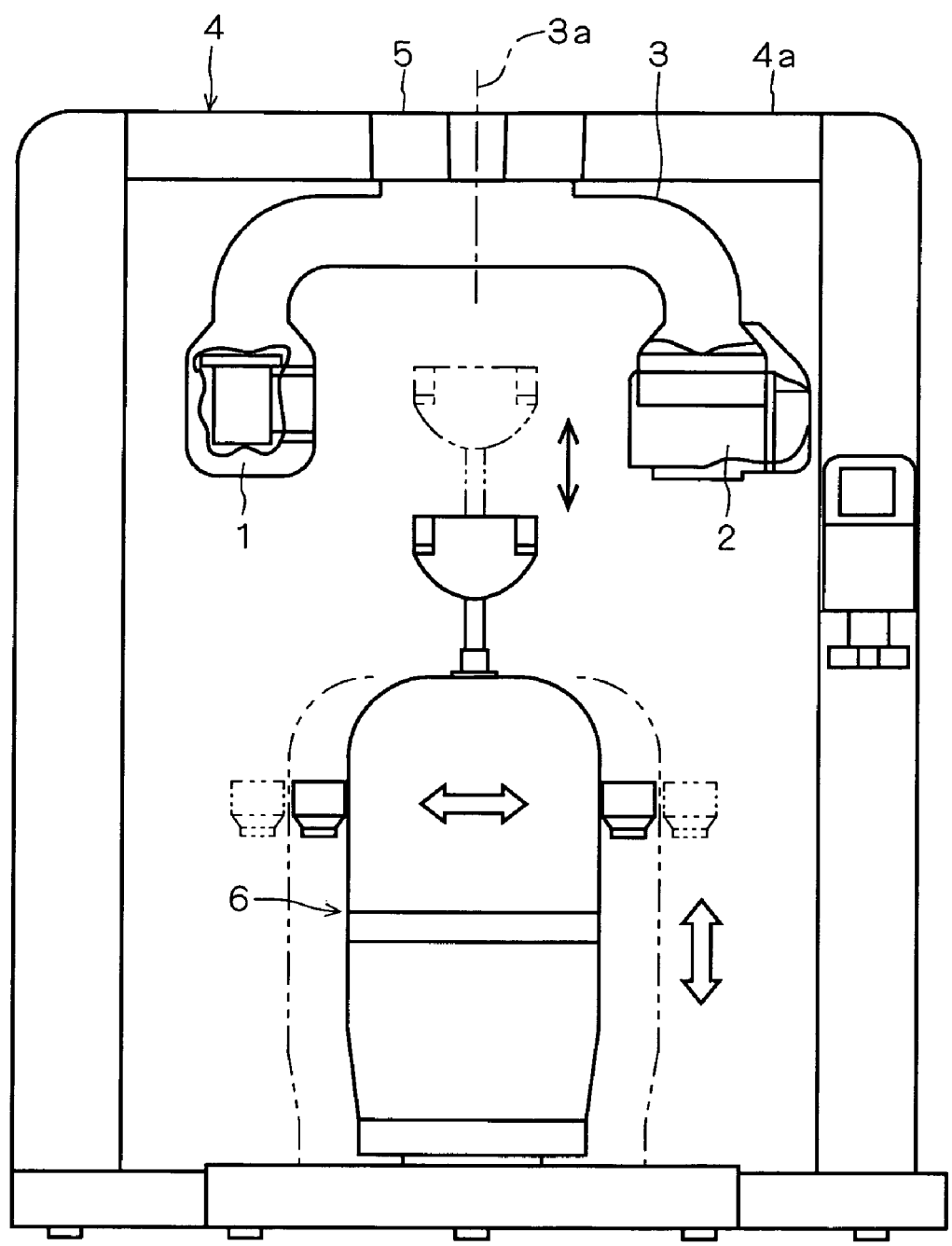
FIGS. 1 and 2 are schematic diagrams showing the X-ray imaging apparatus according to a first embodiment of the present invention.
Figure 2:
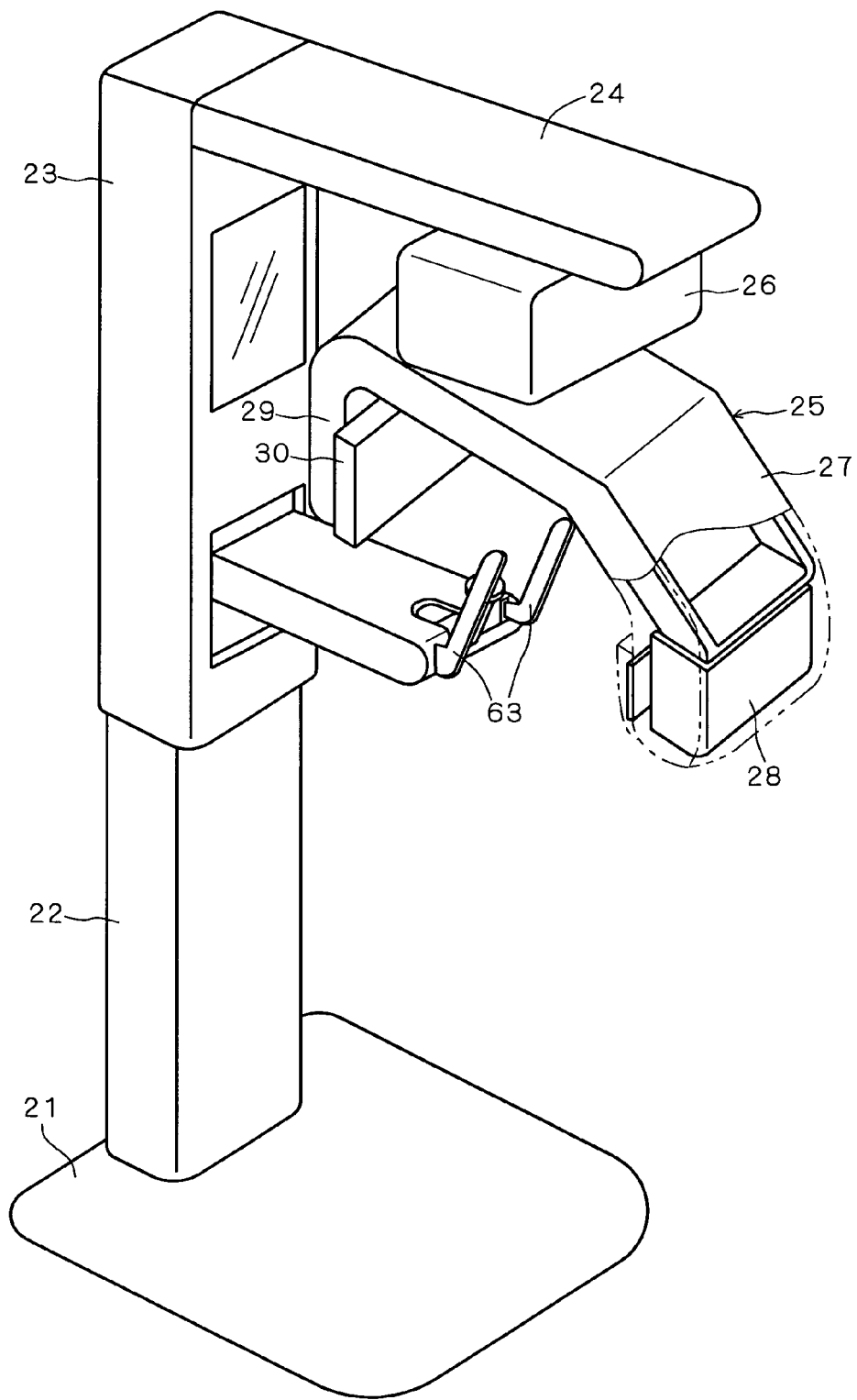

First, the configurations of X-ray imaging apparatuses according to this embodiment are shown in FIGS. 1 and 2. The X-ray imaging apparatus shown in FIG. 1 is for conducting the X-ray computer tomography with an object seated. The X-ray imaging apparatus shown in FIG. 2, on the other hand, is for performing the X-ray computer tomography with the object standing upright. The X-ray imaging apparatus shown in FIG. 1 includes an X-ray source 1 for radiating the X ray, an X-ray image sensor 2 such as a CCD camera and a supporting means 3 for fixing the X-ray source 1 and the X-ray image sensor 2 directed downward at the ends thereof and adapted to rotate around a fixed rotation center 3*a*. The image sensor 2 has a size sufficient to conduct the computer tomography of the head of the object. In order to obtain the panorama tomogram of the dental arch of the object, for example, the image sensor 2 may have the longitudinal size (the length along the direction corresponding to the body axis of the object) of about 14 cm. For computer tomography of the whole head of the object, however, the longitudinal size may be 20 cm to 30 cm and the lateral length 25 cm to 40 cm. The supporting means 3 is mounted on an upper frame 4*a* of a main frame 4 making up a gate-type structure of a very high rigidity, and a rotary drive means 5 mounted on the upper frame 4*a* rotates the supporting means 3 around the rotation center 3*a*. The rotation center 3*a* remains fixed while the computer tomography is performed by rotating the supporting means. However, on the contrary, the rotation center 3*a* may be moved around the rotation center which corresponds to the center of the region of interest of the computer tomography shaping a circle while the computer tomography is performed by rotating the supporting means. In such condition, the X-ray imaging apparatus is able to broaden its imaging region together with so-called "off-set scanning" technology where the X-ray is irradiated only to a part of the region of interest at each irradiation instant. In this case, the rotation drive means 5 may of course be arranged in the supporting means instead of on the upper frame 4*a*.

Further, the X-ray imaging apparatus shown in FIG. 1 includes an object fixing means 6 constituted of a chair in which the object patient is seated. This object fixing means 6 is movable laterally, longitudinally and vertically, and moves the object toward the X-ray imaging target defined by the rotation center 3*a* and the rotary plane height of the supporting means 3. As understood from FIG. 1, the object to be subjected to the X-ray tomography is located between the X-ray source 1 and the X-ray image sensor 2, and the X-ray is radiated from the X-ray source 1 toward the object. The X-ray that has passed through the object is detected by the X-ray image sensor 2. As an alternative to the aforementioned configuration in which the object fixing means 6 is moved, a configuration can be employed in which the supporting means 3 can be moved laterally, longitudinally and vertically together with the rotation center 3*a* thereby to locate the object between the X-ray source 1 and the X-ray image sensor 2. In another alternative configuration, the X-ray source 1 and the X-ray image sensor 2 are fixed by the supporting means 3 in vertically opposed relation to each other in the downward direction. The invention, however, is not limited to these configurations, and any of various other configurations can be employed, including a configuration in which the X-ray source 1 and the image sensor 2 are fixed in opposed relation to each other by the supporting means extended upward from the base of the X-ray imaging apparatus, or a configuration in which a bed-type object fixing means is enveloped by a gantry-type supporting means so that the X-ray source 1 is arranged on a part of the gantry-type supporting means and the X-ray image sensor 2 on another part of the supporting means in opposed relation to the X-ray source 1.

The X-ray imaging apparatus shown in FIG. 2, like the conventional panorama X-ray imaging apparatus for dental application, includes a base 21 mounted on the floor surface, a post 22 arranged on the base 21 and a lift frame 23 adapted to move vertically with respect to the post 22. A horizontal arm 24 is arranged at the upper end of the lift frame 23. The horizontal arm 24 extends forward of the apparatus, i.e. downward to the right in FIG. 2, and a supporting means 25 is mounted at the forward end of the horizontal arm 24. A rotary drive means 26 movable in the longitudinal direction with respect to the horizontal arm 24 (upward to the left in FIG. 1) and in the lateral direction perpendicular to the particular longitudinal direction (upward to the right in FIG. 1) for rotating the supporting means 25 around a rotation axis is arranged between the horizontal arm 24 and the supporting means 25. The rotation center of the supporting means 25 either remains fixed or is moved around during the computer tomographical operation with the supporting means rotated. Incidentally, the apparatus configuration described above is only an example, and a configuration may alternatively be employed in which the rotary drive means 26 is built in the horizontal arm 24 or the supporting means 25.

A first mounting portion 27 extending downward is arranged integrally at an end of the supporting arm 24, and an X-ray source 28 is arranged on the first mounting portion 27. A second mounting portion 29 extending downward is arranged integrally at the other end of the supporting arm 24, and an X-ray image sensor 30 is mounted on the second mounting portion 29. As understood from FIG. 2, the object to be imaged by X-ray is located on an object holding means 63 between the X-ray source 28 and the X-ray image sensor 30, so that the X-ray from the X-ray source 28 is radiated toward the object. The X-ray transmitted through the object is detected by the X-ray image sensor 30.

Figure 3:
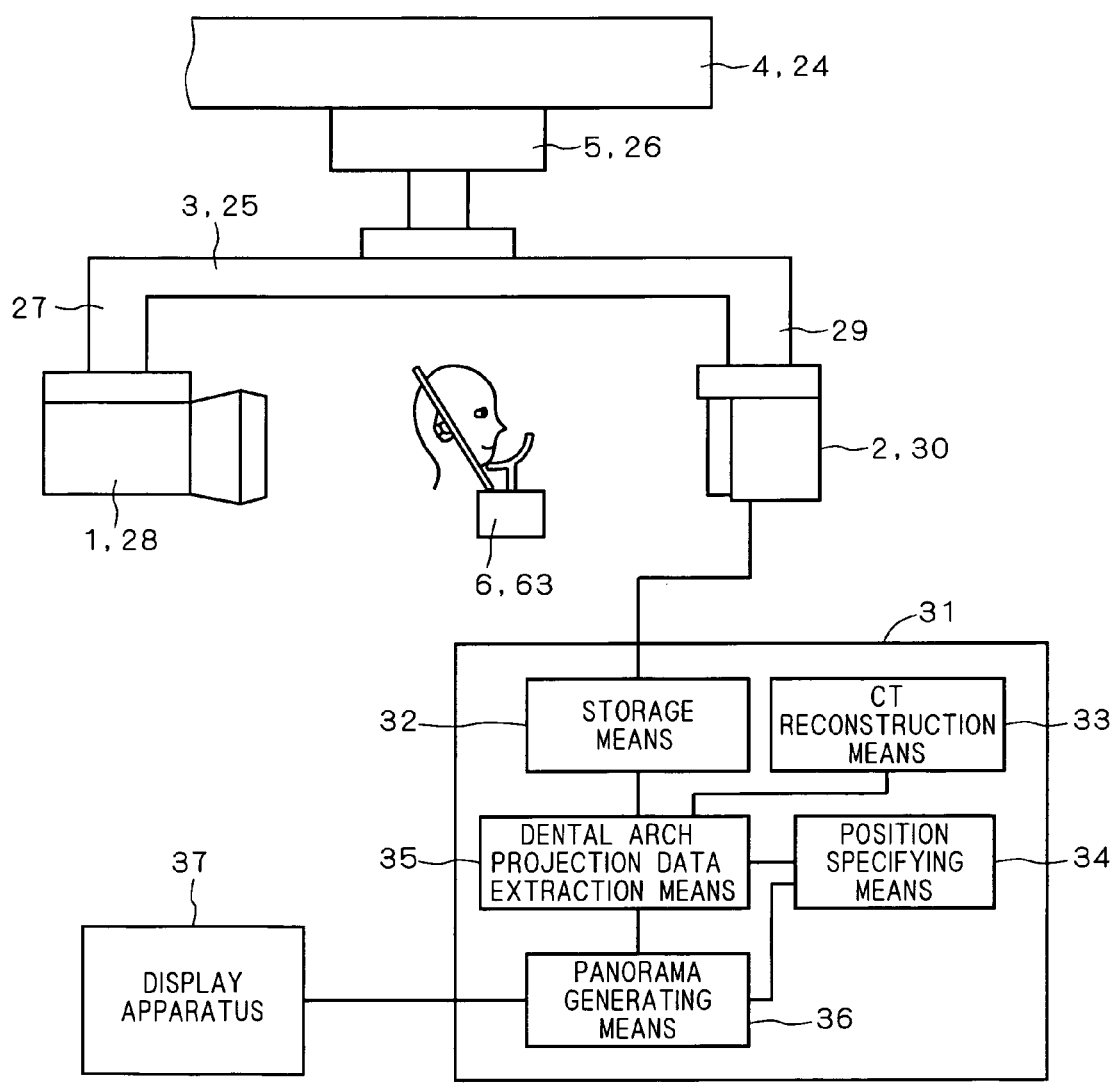
FIG. 3 is a block diagram showing the X-ray imaging apparatus according to the first embodiment of the present invention.

FIG. 3 is a block diagram showing the X-ray imaging apparatus according to this embodiment. In the block diagram of FIG. 3, the X-ray is radiated from the X-ray source 1, 28 toward the head of the object set in position by the object fixing means 6 or the object holding means 63, and after being passed through the object, detected by the X-ray image sensor 2, 30, which in turn generates and outputs the X-ray projection data. The X-ray projection data output from the X-ray image sensor 2, 30 is input to an image processing apparatus 31. In the image processing apparatus 31, the input X-ray projection data is stored in a storage means 32 such as a HDD. Further, the image processing apparatus 31 includes a CT reconstruction means 33 for generating a three-dimensional volume data by CT reconstruction of the X-ray projection data by reverse projection using a filter, a position specifying means 34 for specifying the position of the dental arch of the object in the X-ray projection data, a dental arch projection data extraction means 35 for extracting the dental arch projection data corresponding to the dental arch from the X-ray projection data based on the position information of the dental arch obtained by the position specifying means 34 and a panorama generating means 36 for generating the panorama tomogram by executing a predetermined process using the dental arch projection data.

Figure 4:
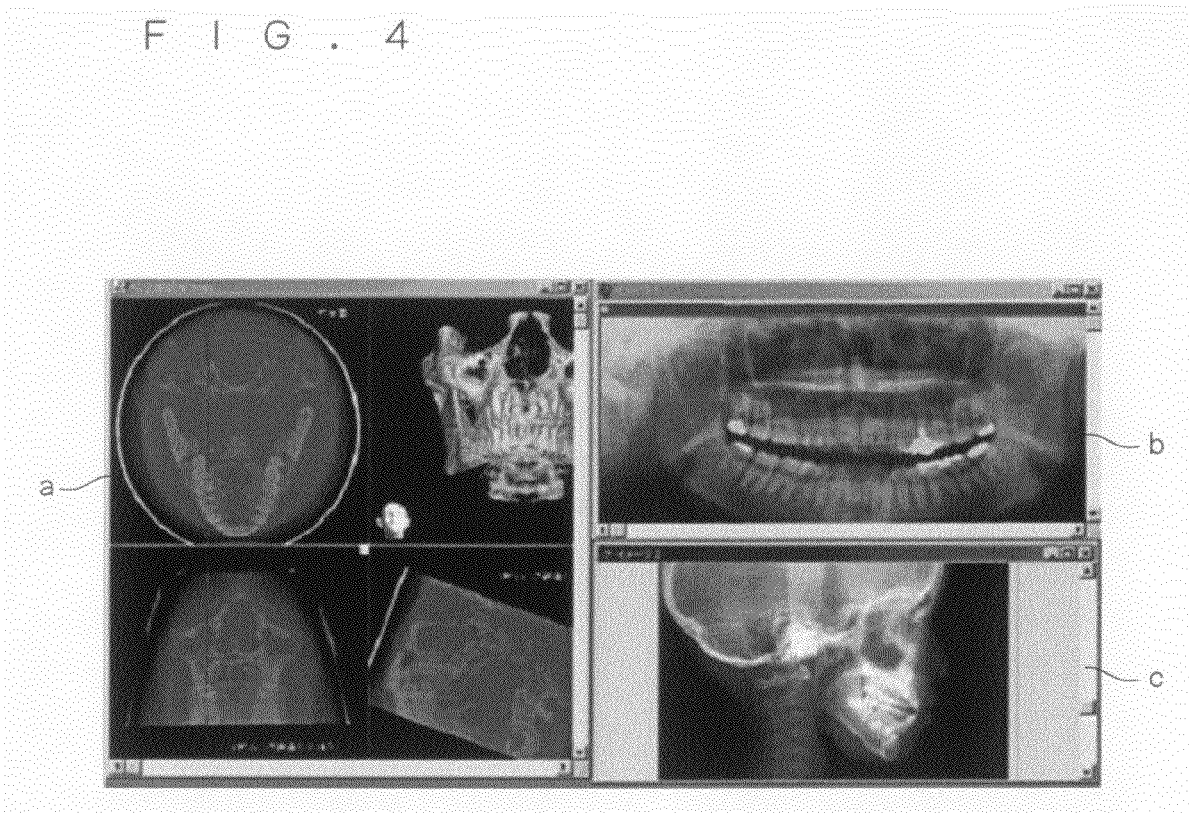
FIG. 4 is a diagram showing an example of the display image on the X-ray imaging apparatus according to the first embodiment of the present invention.

The panorama tomogram generated by the image processing apparatus 31 is stored in the storage means 32 while at the same time being displayed on a display apparatus 37. FIG. 4 shows an example of screen displayed in the display apparatus 37. In the display example shown in FIG. 4, a CT image "a" sliced into sectional views taken from three directions orthogonal to each other after CT reconstruction is displayed on the left side in the screen, a panorama tomogram "b" on the upper right side of the screen and an X-ray transmitted image "c" of the side surface of the dentomaxillofacial region on the lower right side of the screen. Although the three images including the CT image "a", the panorama tomogram "b" and the X-ray transmitted image "c" are displayed at the same time, only the panorama tomogram b may be displayed according to the present invention. Also, according to this invention, the panorama tomogram "b" is displayed before or at the same time as the CT image "a". In other words, the panorama tomogram "b" is displayed before the images other than the panorama tomogram "b" obtained by computer tomography or at the same time as at least one image other than the panorama tomogram "b". In this way, the dentist can first confirm the panorama tomogram "b" to which he/she is accustomed, and from this panorama tomogram "b", can proceed to the CT image "a" of the required part, thereby making efficient diagnosis possible.

In the aforementioned configuration according to this embodiment, the image processing apparatus 31 and the display apparatus 37 are integrally arranged with the X-ray imaging apparatus. This configuration may be replaced, however, with a configuration in which the image processing apparatus 31 and the display means 37 are arranged independently of the X-ray imaging apparatus.

(Method of Generating Panorama Tomogram)

Next, a predetermined process for generating the panorama tomogram in the panorama generating means 36 is explained. According to this embodiment, the dental arch projection data required for generating the panorama image is extracted by the dental arch projection data extraction means 35 from the X-ray projection data obtained by the X-ray computer tomography, and any of the following processes is executed using the particular dental arch projection data thereby to generate the panorama image.

Figure 5:
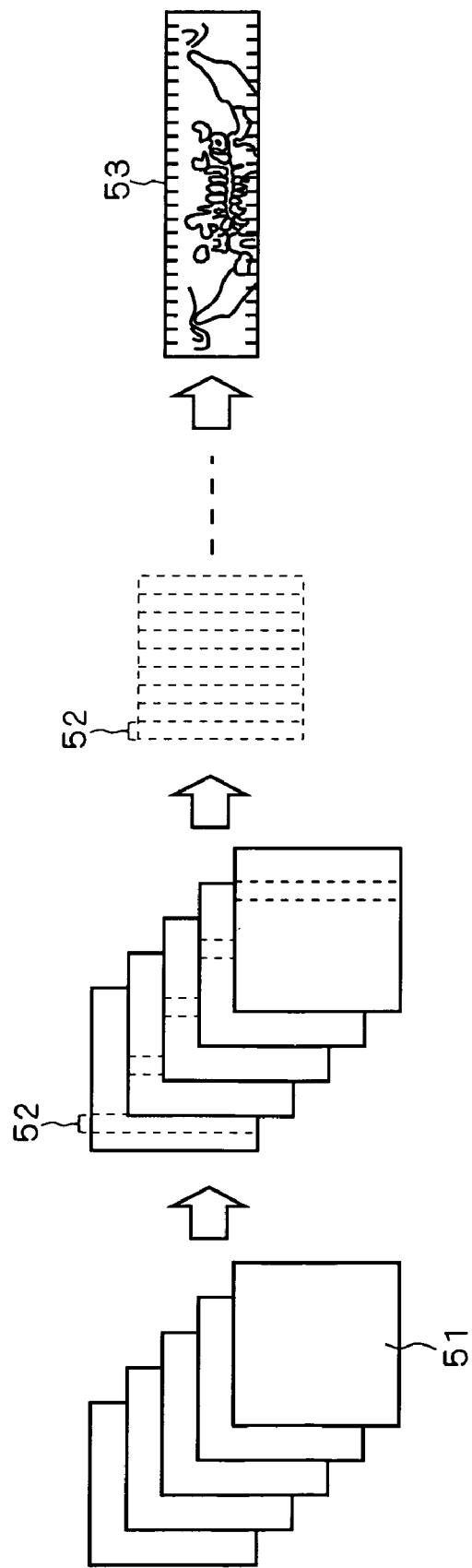
FIGS. 5 and 6 are diagrams describing the image processing method according to the first embodiment of the present invention.

In the direct process constituting the first process, that part of the dental arch projection data extracted from the dental arch projection data extraction means 35 which makes up the panorama tomogram is extracted in strips, and by connecting the strips of images to each other, the panorama tomogram is generated. FIG. 5 is a schematic diagram showing the direct process. In FIG. 5, the first step is to produce a plurality of X-ray projection data 51 having an area of such a size as to cover the dentomaxillofacial region by the X-ray computer tomography, and the dental arch projection data is extracted from the X-ray projection data 51 based on the positional information of the dental arch obtained by the position specifying means 34. Then, the part of the dental arch projection data making up the panorama tomogram is extracted in strips (the image 52 in strips). After that, the strips of the image 52 thus extracted are connected based on the positional information of the dental arch obtained by the position specifying means 34 thereby to generate one panorama tomogram 53. Incidentally, any of various sensors such as the CCD sensor or MOS sensor can be used as the X-ray image sensor to obtain the X-ray projection data 51. In the case where the CCD sensor is used, for example, the X-ray projection data for subsequent CT reconstruction and the strips of image data for generating the panorama tomogram may be stored in separate frame memories. In the case where the MOS sensor is used, on the other hand, a plurality of X-ray projection data may be stored in a single frame memory as a collection of dynamic images.

In the presence of the image data on the dental arch portion shared by the plural strips of images 52, the strips of images 52 are connected by superimposing the common parts of the image data one on another thereby to generate the panorama tomogram 53. Incidentally, the method of generating the panorama tomogram 53 by superposing and connecting the X-ray projection data one on another disclosed in Paragraph 0037 or 0038, FIG. 11 or 12 of the specification of Japanese Patent Application Laid-Open No. 8-257026, for example, may be employed, in which the object images other than the layer surfaces are buried in the background by being superimposed one on another. Another employable example of the method of generating the panorama tomogram by extracting and connecting the image data is disclosed in Japanese Patent Application Laid-Open No. 2000-57789, in which the panorama tomogram is generated using the ortho-X-ray cone beam.

In the direct process, the panorama tomogram 53 can be generated directly without CT reconstruction of the X-ray projection data 51, and therefore, the processing time and the processing capacity required for CT reconstruction can be saved advantageously. Also, in view of the fact that the panorama tomogram 53 is generated by the direct process without CT reconstruction, the metal artifact of which the metal portion mounted on the dentition otherwise might have an effect on the adjacent portions due to the CT reconstruction is prevented from intruding into the panorama tomogram 53.

Figure 6:
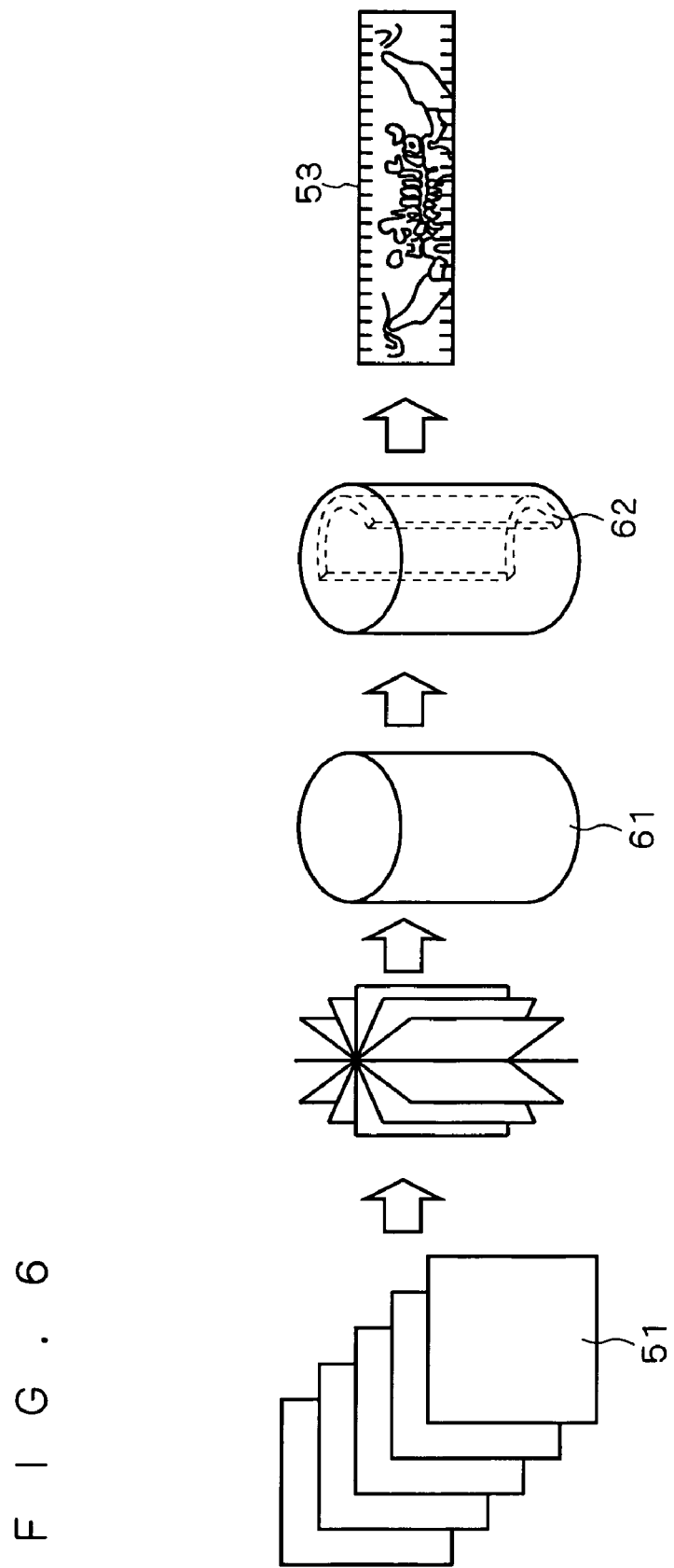

In the second process, i.e. the reconstruction process, the dental arch projection data is extracted by the dental arch projection data extraction means 35 from the three-dimensional volume data obtained by CT reconstruction of the X-ray projection data. Then the panorama tomogram is generated using the dental arch projection data thus extracted. FIG. 6 is a schematic diagram showing the reconstruction process. In FIG. 6, the first step is to produce a plurality of X-ray projection data 51 by X-ray computer tomography, and the three-dimensional volume data 61 is obtained by CT reconstruction of the X-ray projection data 51. From this three-dimensional volume data 61, the dental arch projection data 62 is extracted by the dental arch projection data extraction means 35, and using this dental arch projection data 62, the portion required for the panorama tomogram is extracted thereby to generate the panorama tomogram 53.

In the method using the CT reconstruction process, the three-dimensional volume data 61 is produced by CT reconstruction of the X-ray projection data 51, and from this three-dimensional volume data 61, the panorama tomogram is generated. As compared with the panorama tomogram obtained by the direct process, therefore, the image data on such parts as the cervical vertebra other than the dental arch is prevented from intruding into the panorama tomogram. Also, in displaying the image obtained by computer tomography as a CT image, the CT reconstruction is an indispensable process. Thus, the three-dimensional volume data generated by a single CT reconstruction process is used also for generating the panorama tomogram, thereby contributing to the effective use of the image data. Although the method of generating the panorama tomogram according to the present invention is explained above, embodiments of the present invention are not limited to the generation of the panorama tomogram of the whole chin as shown in FIGS. 5, 6. By the partial computer tomography using a part of the X-ray image sensor, for example, the X-ray projection data on a part of the dental arch may be acquired, or by using a part of the X-ray projection data acquired by computer tomography on the whole head, the panorama tomogram limited in range to the upper jaw, lower jaw or the jaw joint can be generated and displayed.

(Image Processing Method)

Figure 7:
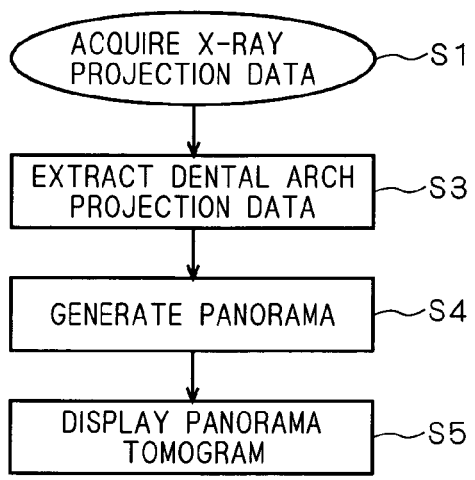
FIGS. 7 and 8 are flowcharts showing the image processing method according to the first embodiment of the present invention.

Next, the image processing method according to this embodiment is explained with reference to FIGS. 7 and 8. FIG. 7 shows the image processing method for generating the panorama tomogram by the direct process, and FIG. 8 the image processing method for generating the panorama tomogram by the reconstruction process. According to this embodiment, the X-ray projection data 51 is obtained by computer tomography, after which the panorama tomogram can be generated without any operation or simply by depressing one button. The latest anatomical analysis shows that what may be called a reference dental arch T' for the dental arch T illustrated in FIG. 9 is found to have the standard position and shape in the head. By holding the head of the object by the object holding means of the X-ray computer tomograph, therefore, the position and shape of the reference dental arch T' in the imaging area A of the X-ray computer tomography or the position and shape of the reference dental arch T with respect to the center C of the imaging area A can be automatically determined. In the case where the X-ray computer tomograph is manufactured in a factory taking advantage of this fact, for example, the position and shape of the reference dental arch T' are stored in the storage means 32 before final shipment, and these reference position and shape can be read and used as a default data in generating the panorama tomogram. First, in FIG. 7, the X-ray projection data is obtained in step S1 by the X-ray computer tomography of the dentomaxillofacial region of the object using the X-ray imaging apparatus shown in FIGS. 1 and 2. Next, in the dental arch projection data extraction step S3, the dental arch projection data extraction means 35 reads the information on the position and shape of the reference dental arch T stored in the storage means 32, and based on this information, extracts the dental arch projection data corresponding to the dental arch from the X-ray projection data. Incidentally, a plurality of patterns of the position or shape may be prepared in addition to the position and shape of the reference dental arch T' stored and any of such patterns may be selected subsequently.

In the dental arch projection data extraction step S3, the dental arch projection data may be extracted by reference to the information on at least one of the X-ray incidence angle to the dental arch and the layer thickness. Since the X-ray incidence angle and the layer thickness can be freely selected, the desired panorama tomogram can be obtained. Incidentally, the X-ray incidence angle and the layer thickness can be set either before or after X-ray computer tomography.

In the next panorama generating step S4, the panorama generating means 36 generates the panorama tomogram by the aforementioned direct process using the dental arch projection data. In the panorama tomogram display step S5, the panorama tomogram generated is displayed on the display apparatus 37.

Figure 8:
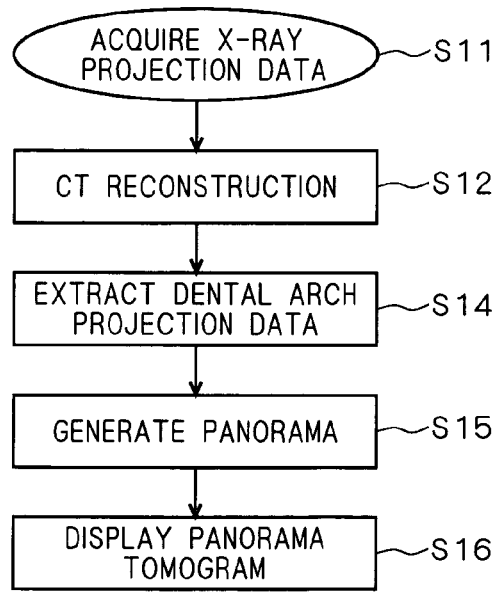
Figure 9:
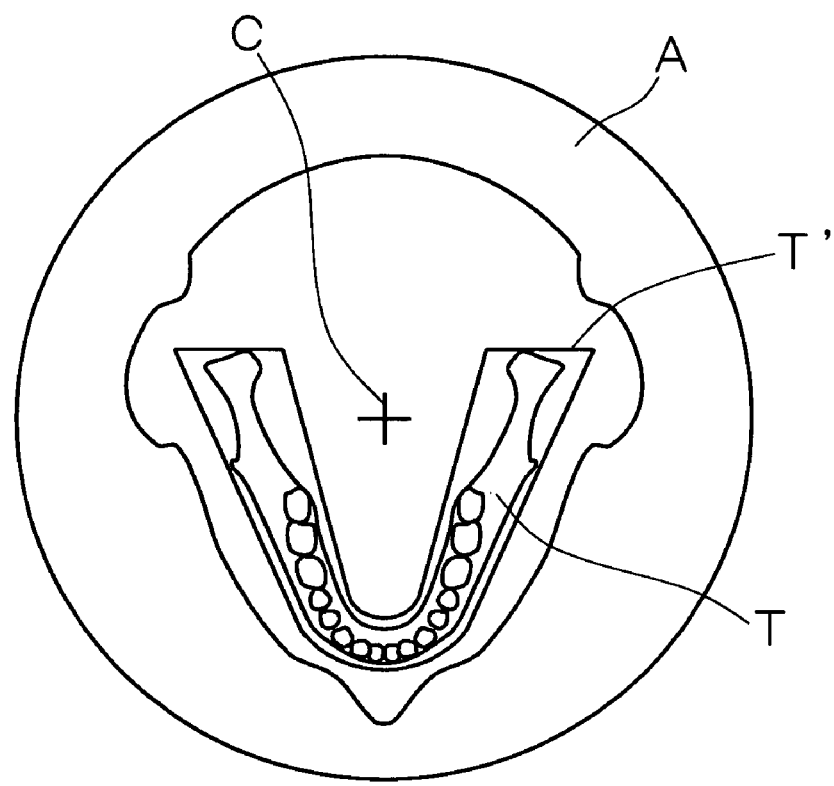
FIG. 9 is a schematic diagram showing an example of the position and the shape of a standard dental arch assumed in the image processing method according to the first embodiment of the present invention.

In step S11 of the image processing method shown in FIG. 8, on the other hand, the X-ray projection data is obtained by X-ray computer tomography on the dentomaxillofacial region of the object using the X-ray imaging apparatus shown in FIGS. 1 and 2. Next, in the CT reconstruction step S12, the three-dimensional volume data is obtained by CT reconstruction of the X-ray image data by the CT reconstruction means 33.

Next, in the dental arch projection data extraction step S14, the dental arch projection data extraction means 35 reads the information on the position and shape of the reference dental arch T' stored in the storage means 32, and based on this information, extracts the dental arch projection data corresponding to the dental arch from the X-ray projection data (three-dimensional volume data) subjected to CT reconstruction. Incidentally, a plurality of position or shape patterns may be prepared in addition to the position and shape of the reference dental arch T stored and any of them may be selected subsequently. Also, in the dental arch projection data extraction step S14, the dental arch projection data may be extracted with reference to the information on at least one of the X-ray incidence angle to the dental arch and the layer thickness.

Figure 10:
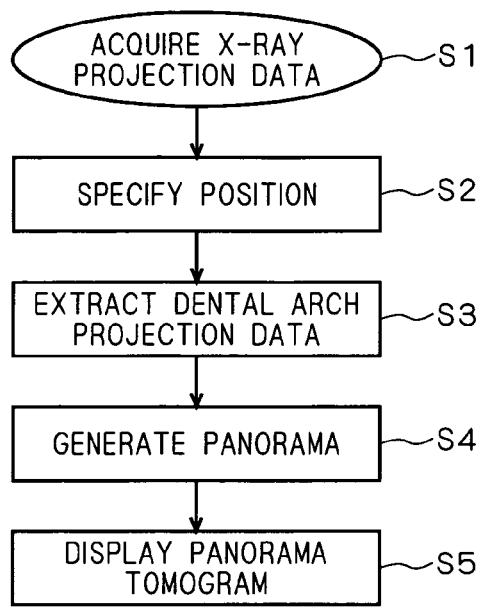
FIGS. 10 and 11 are flowcharts showing the image processing method according to another example of the first embodiment of the present invention.

In the panorama generating step S15, the panorama generating means 36 of the image processing apparatus 31 generates the panorama tomogram by executing the aforementioned reconstruction process using the dental arch projection data. In the panorama tomogram display step S16, the panorama tomogram generated is displayed on the display apparatus 37. As another example of this embodiment, the image processing method including the step of specifying the position of the dental arch using the position specifying means 34 to produce the panorama tomogram higher in accuracy is explained with reference to FIGS. 10 and 11. FIG. 10 shows the image processing method for generating the panorama tomogram by the direct process, and FIG. 11 the image processing method for generating the panorama tomogram by the reconstruction process. First, the flowchart of FIG. 10 is basically identical with the flowchart of FIG. 7 except that the position specifying step S2 is added in FIG. 10, and therefore, the same steps are designated by the same reference numerals, respectively, and not described in detail. With reference to the flowchart shown in FIG. 10 in the position specifying step S2, the position specifying means 34 specifies the position of the dental arch of the object in the X-ray projection data. In the dental arch projection data extraction step S3, the dental arch projection data extraction means 35, based on the positional information on the dental arch in the X-ray projection data obtained in the position specifying step S2, extracts the dental arch projection data corresponding to the dental arch from the X-ray projection data. The dental arch projection data extraction step S3 according to this embodiment uses a predetermined shape of the dental arch in extracting the dental arch projection data. Incidentally, the shape of the dental arch may be selected from a plurality of shape patterns.

The flowchart shown in FIG. 11, on the other hand, is basically identical with the flowchart shown in FIG. 8 except that the position specifying step S13 is added to FIG. 11, and therefore, the same steps are designated by the same reference numerals, respectively, and not described in detail below. Also in the position specifying step S13 of the flowchart shown in FIG. 11, the position specifying means 34 specifies the whereabouts of the dental arch of the object in the X-ray projection data. Incidentally, in the position specifying step S13, the whereabouts of the dental arch of the object may be specified in the X-ray projection data subjected to CT reconstruction (three-dimensional volume data). In the dental arch projection data extraction step S14, the dental arch projection data corresponding to the dental arch is extracted by the dental arch projection data extraction means 35 from the X-ray projection data subjected to CT reconstruction (three dimensional volume data) based on the position information of the dental arch in the X-ray projection data obtained in the position specifying step S13. In the dental arch projection data extraction step S14 according to this embodiment, the dental arch projection data is retrieved using a predetermined shape of the dental arch. Nevertheless, any one may be selected from a plurality of shape patterns of the dental arch.

(Specific Example of Position Specifying Step)

Next, a specific example of the position specifying step to determine the position of the dental arch of the object in the X-ray projection data is explained.

Figure 12:
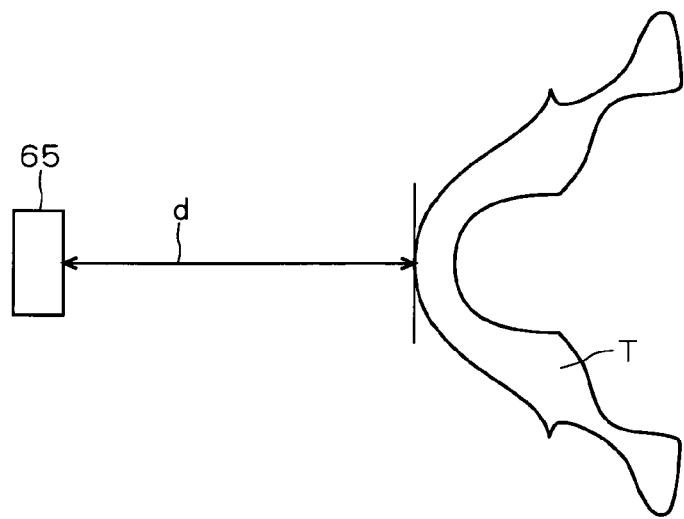
FIGS. 12, 13 and 14 are diagrams describing specific cases of the position specifying steps in the image processing method according to another example of the first embodiment of the present invention.

First, an explanation is given about an example of specifying the position of the dental arch of the object from the distance information between the object or the imaging aid mounted on the object and the X-ray imaging apparatus at the time of X-ray computer tomography. In this example, a position detection sensor 65 mounted on the X-ray imaging apparatus, as shown in FIG. 12, detects the distance d to the front teeth of the dental arch T of the object. Based on the detected distance d, the position specifying step specifies the position of the dental arch with respect to the X-ray imaging apparatus, and the dental arch projection data corresponding to the dental arch is retrieved from the X-ray projection data in the dental arch projection data extraction step. As an alternative, an imaging aid may be mounted on the object (the front teeth, for example) and a sensor responsive to the aid mounted on the X-ray imaging apparatus to detect the distance to the dental arch of the object. As another alternative, after the position of the dental arch with respect to the X-ray imaging apparatus is specified by the position detection sensor 65, the rotation center 3a of the rotary drive means 5 may be moved in accordance with the position of the dental arch or, without moving the rotation center 3a, the whole head of the object may be subjected to the X-ray computer tomography, and the dental arch projection data may be extracted for the dental arch position specified in the acquired X-ray projection data of the whole head. In the latter case, the dental arch position with respect to the X-ray computer tomography apparatus may be specified based on the distance d, so that the panorama tomogram can be obtained by changing only the dental arch position in the whole X-ray projection data without changing the range in which the X-ray projection data is acquired. According to this example, the existing position detection sensor and the imaging aid can be used and the position of the dental arch can be automatically specified easily and inexpensively.

Figure 13:
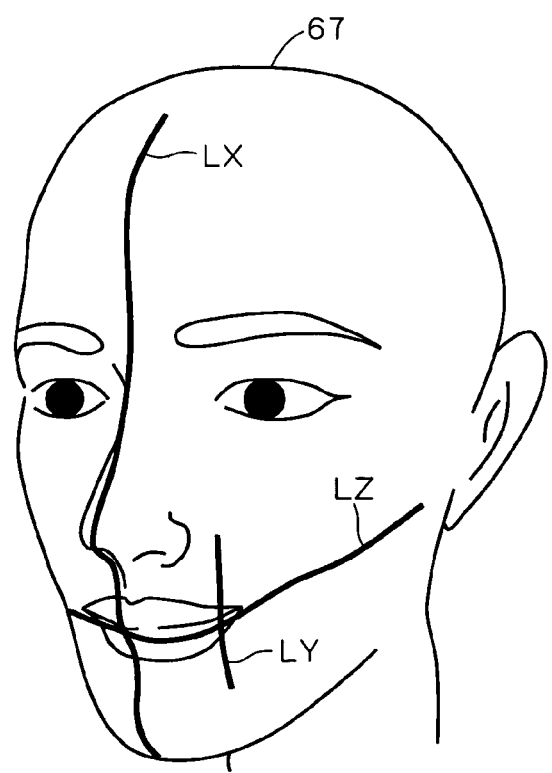

Next, an explanation is made about an example in which the positioning beams are radiated on the object at the time of X-ray computer tomography to specify the dental arch position of the object from the beam position information. In this example, as shown in FIG. 13, the positioning beams LX, LY, LZ are radiated on the face of the object 67. The positioning beams LX, LY, LZ are radiated on the surface of the object 67 to enable the operator to confirm the position at which the object 67 is located. Also, the dental arch position with respect to the X-ray imaging apparatus is preset in the X-ray imaging apparatus, and the object is set in position using the positioning beams LX, LY, LZ in such a manner that the set dental arch position coincides with the dental arch of the object. Then, the X-ray imaging apparatus performs the X-ray computer tomography at the particular position thus set as the dental arch position. Once the object 67 is set in position using the positioning beams LX, LY, LZ, the dental arch of the object 67 can be set in position at the proper dental arch position preset for the X-ray imaging apparatus to acquire the X-ray projection data. Thus, the position of the dental arch of the object 67 with respect to the X-ray imaging apparatus can be estimated and specified. Conversely, after holding the object in the object holding means, the radiation positions of the positioning beams LX, LY, LZ may be moved into coincidence with the object, and based on the amount of movement of the radiation position of each positioning beams, the position of the dental arch to be imaged by the X-ray imaging apparatus may be reconfigure. In the case where the dental arch position is reconfigure in this way, the rotation center 3a of the rotary drive means 5 may be moved. Or, without moving the rotation center 3a, the whole head of the object may be subjected to the X-ray computer tomography, and at the time point when the projection data of the dental arch is extracted from the acquired X-ray projection data, the dental arch position may be reconfigure and the data extracted using the information on the radiation position of the positioning beams. As described above, according to this embodiment, the method similar to that for the conventional dental panorama X-ray imaging apparatus can be used with equal effect, and therefore, the dental arch can be set in position easily without mastering the operation of a separate apparatus.

Figure 14:
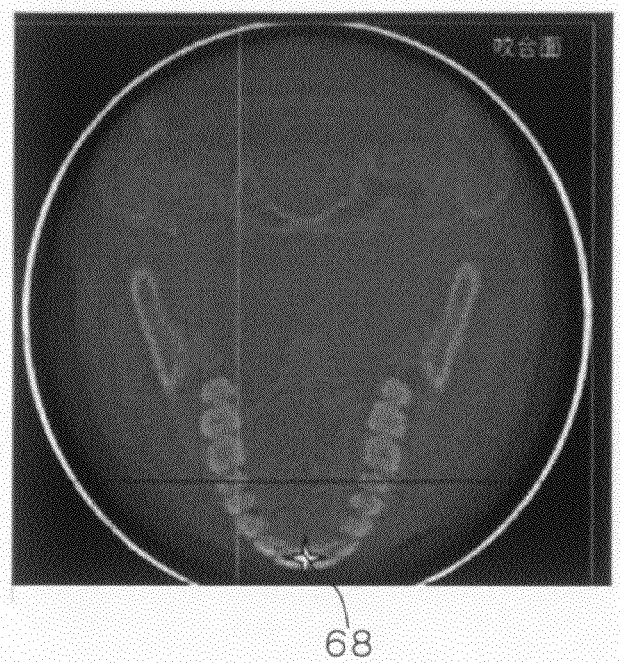

Now, an example is explained in which the image of the dental arch is displayed based on the three-dimensional volume data obtained by CT reconstruction of the X-ray projection data, and according to the input signal designating one reference point in the dental arch image, the position of the dental arch of the object is specified. In this example, the position of the front tooth, for example, is designated and input as a reference point from the dental arch image (CT image) (FIG. 14) based on the three-dimensional volume data obtained by CT reconstruction of the X-ray projection data. Incidentally, FIG. 14 shows a CT image of the occlusal surface and shows the selected front tooth as a mark 68. The reference point is designated by clicking the position of the front tooth on the CT image or by inputting the coordinate of the front tooth directly from the keyboard (not shown). The reference point is not limited to the front tooth, but may be the left or right canine tooth or one of the left and right ends of the dental arch. The reference point thus designated is used as the X, Y coordinate information as shown in FIG. 14 in the dental arch projection data extraction step. This example requires no additional device and has the advantage that the dental arch can be confirmed and the position thereof specified on the CT image.

As explained above, in the image processing method according to this embodiment, the panorama tomogram of the dental arch can be easily obtained from the X-ray projection data produced in the X-ray computer tomography by storing the position and shape of the reference dental arch of the object or simply by specifying the dental arch position with a simple mechanism or operation after storing the reference dental arch shape. Incidentally, according to this embodiment, the image processing method is explained with reference to the flowcharts of FIGS. 7, 8, 10 and 11. Nevertheless, this invention is not limited to such an embodiment, but a program for computer operation may be employed as a means of executing the image processing method according to the flowchart shown in FIGS. 7, 8, 10 and 11. Also, according to this invention, a storage medium for storing the particular program (such as a program stored in a hard disk) may be employed. Further, the computer-readable storage medium for storing the program may be, for example, a CD-ROM or MO other than the hard disk.

Second Embodiment (General Description)

This embodiment of the present invention also relates to an image processing method capable of acquiring the panorama tomogram easily of the dental arch using the X-ray projection data on the dentomaxillofacial region obtained by the X-ray computer tomography, and an image processing apparatus and an X-ray imaging apparatus for implementing the method. According to this embodiment of the present invention, however, unlike the first embodiment of the present invention for acquiring the panorama tomogram based on the shape of the dental arch preset as an anatomical reference, is further intended to specify the shape of the dental arch.

(Configuration of X-Ray Imaging Apparatus and Image Processing Method)

Figure 15:
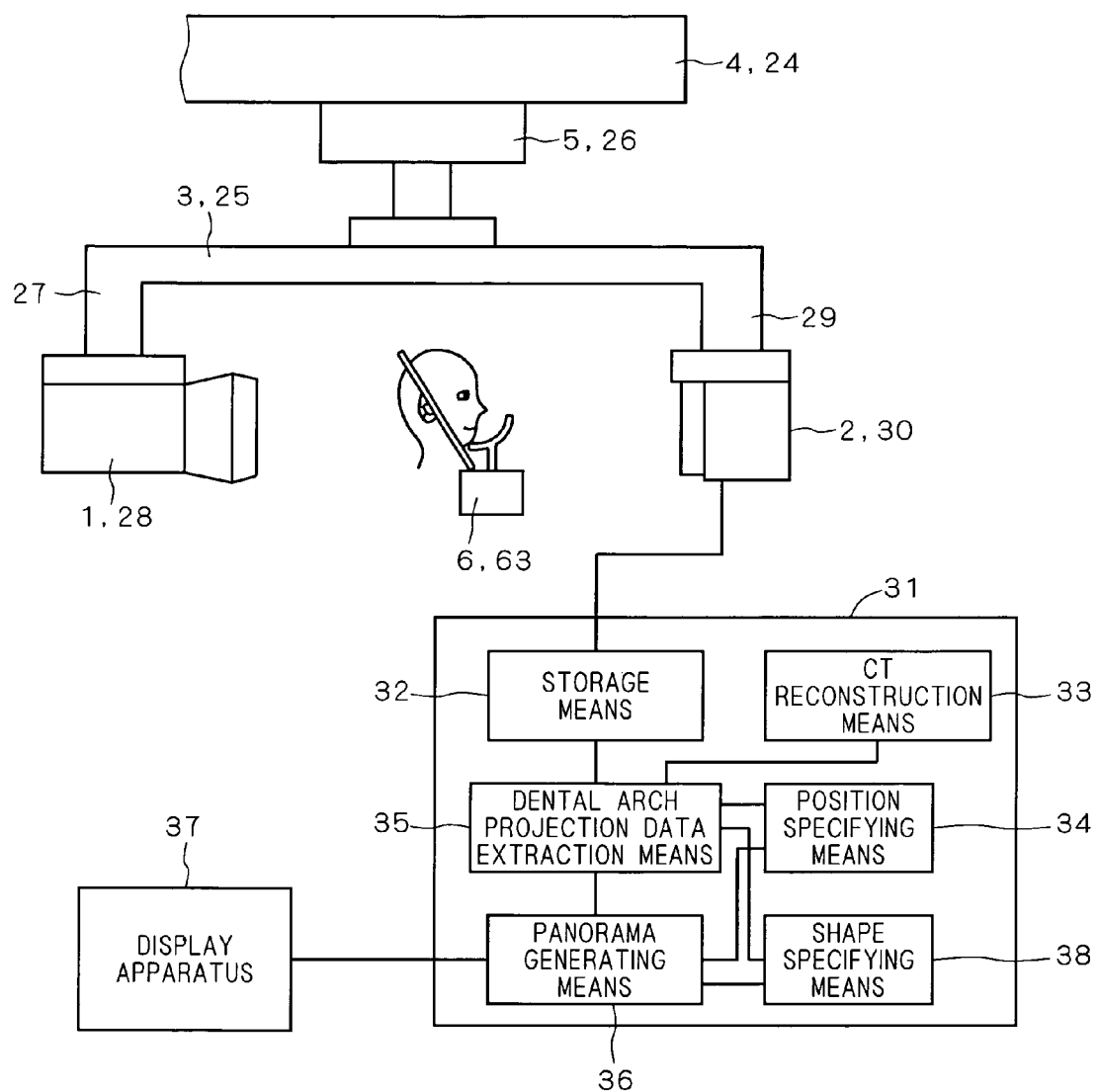
FIG. 15 is a block diagram showing the X-ray imaging apparatus according to a second embodiment of the present invention.

FIG. 15 is a block diagram showing the X-ray imaging apparatus according to this embodiment. The block diagram of FIG. 15 is basically identical with the block diagram of FIG. 3 except that the shape specifying means 38 is added to the image processing apparatus 31 in the present embodiment. Therefore, the same component elements are designated by the same reference numerals, respectively, and not described in detail below. In the X-ray imaging apparatus according to this embodiment, the shape specifying means 38 specifies the shape of the dental arch of the object in the X-ray projection data, and the dental arch projection data extraction means 35 retrieves the dental arch projection data corresponding to the dental arch from the X-ray projection data based on the position and shape information acquired by the position specifying means 34 and shape specifying means 38.

Figure 16:
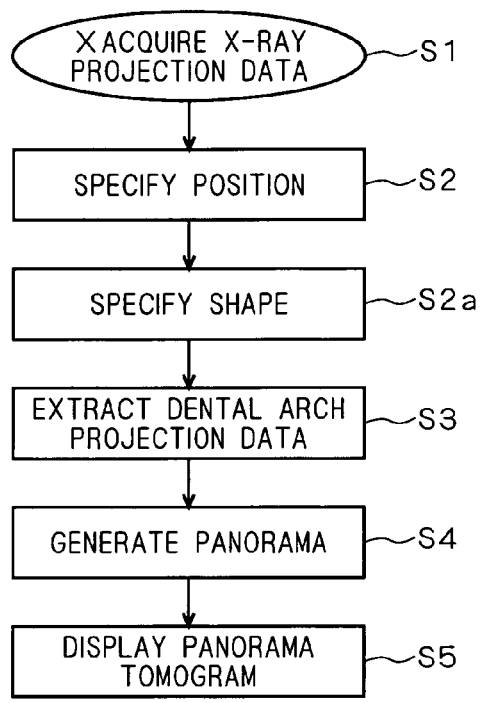
FIGS. 16 and 17 are flowcharts showing the image processing method according to the second embodiment of the present invention.

Next, the image processing method according to this embodiment is explained with reference to FIGS. 16 and 17. FIG. 16 shows the image processing method for generating the panorama tomogram by the direct process, and FIG. 17 the image processing method for generating the panorama tomogram by the reconstruction process. First, the flowchart shown in FIG. 16 is basically identical with that of FIG. 10 except that the shape specifying step S2a is added to the former. Therefore, the same steps are designated by the same reference numerals, respectively, and not described in detail below. In the flowchart shown in FIG. 16, the shape of the dental arch of the object in the X-ray projection data is specified by the shape specifying means 38 in the shape specifying step S2a. Then, in the dental arch projection data extraction step S3, the dental arch projection data corresponding to the dental arch is retrieved from the X-ray projection data based on the dental arch position and shape information in the X-ray projection data obtained in the position specifying step S2 and the shape specifying step S2a.

Figure 11:
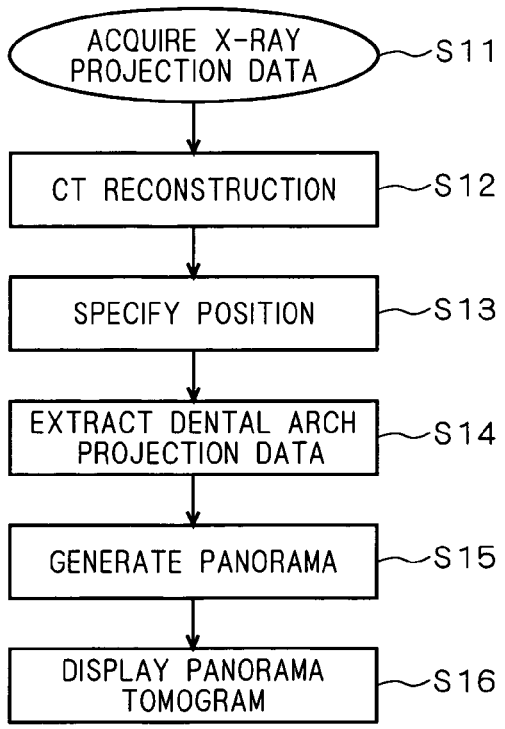
Figure 17:
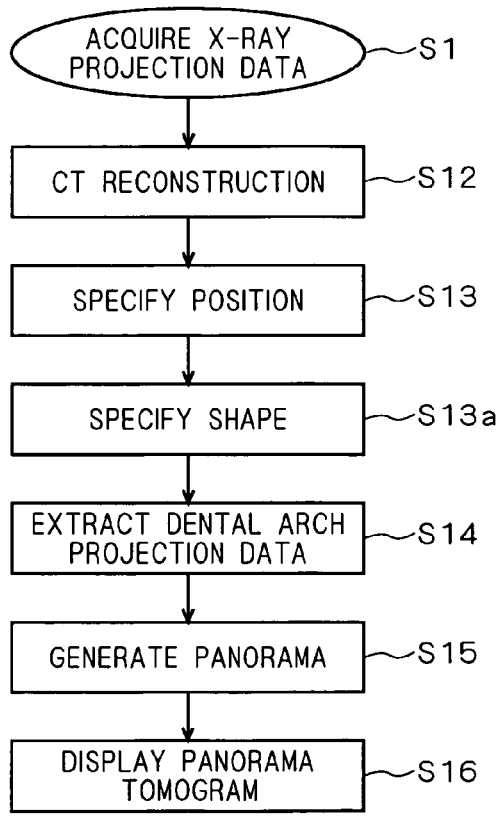

The flowchart shown in FIG. 17 is basically identical with the flowchart shown in FIG. 11 except that the shape specifying step S13a is added to the former. Therefore, the same steps are designated by the same reference numerals, respectively, and not described in detail again. Also in the flowchart shown in FIG. 17, the shape of the dental arch of the object in the X-ray projection data is specified by the shape specifying means 38 in the shape specifying step S13a. Incidentally, the X-ray projection data dealt with in the shape specifying step S13a may be the one (three-dimensional volume data) subjected to CT reconstruction. Then, the dental arch projection data corresponding to the dental arch is retrieved in the dental arch projection extraction step S14 from the X-ray projection data (three-dimensional volume data) subjected to CT reconstruction based on the position and shape information of the dental arch in the X-ray projection data obtained in the position specifying step S13 and the shape specifying step S13a.

(Specific Example of Position Specifying Step and Shape Specifying Step)

Figure 18:
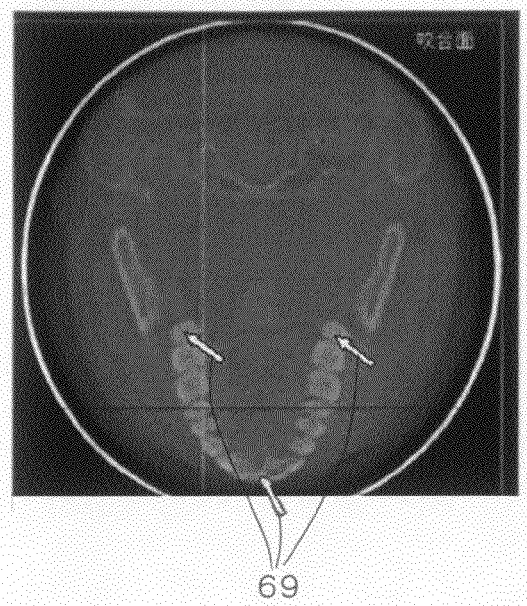

Next, a specific example of the position specifying step for specifying the whereabouts of the dental arch of the object and the shape specifying step for specifying the shape of the dental arch of the object in the X-ray projection data is explained below. First, an example is explained in which the image of the dental arch is displayed based on the three-dimensional volume data obtained by CT reconstruction of the X-ray projection data so that the position and shape of the dental arch of the object are specified based on the input designating a plurality of reference points in the dental arch image. In this example, three reference points representing the positions of the front tooth and the back teeth on the two sides are designated from the dental arch image (CT image) (FIG. 18) based on the three-dimensional volume data obtained by CT reconstruction of the X-ray projection data. In FIG. 18 showing the CT image of the occlusal surface, the front tooth and the back teeth selected on the two sides are indicated by arrows 69. This designation may be made by clicking the position of the front tooth on the CT image or by directly inputting the coordinates of the front tooth and the back teeth on the two sides by way of the keyboard and the like. The reference points designated are not limited to the three points including the front tooth and the back teeth on the two sides or not to three in number, but may be any plurality of points from which information for specifying the position and shape of the dental arch can be secured.

According to this example, the shape of the dental arch is specified by the spline process or the like based on a plurality of reference points designated. By increasing the number of the reference points designated, therefore, the shape of the dental arch can be specified with higher accuracy. In other words, the accuracy with which the shape of the dental arch is specified and the number of the reference points designated is in the relation of tradeoff with each other. In this embodiment, no device is required to be added and the position of the dental arch can be specified by confirming it on the CT image.

Figure 19:
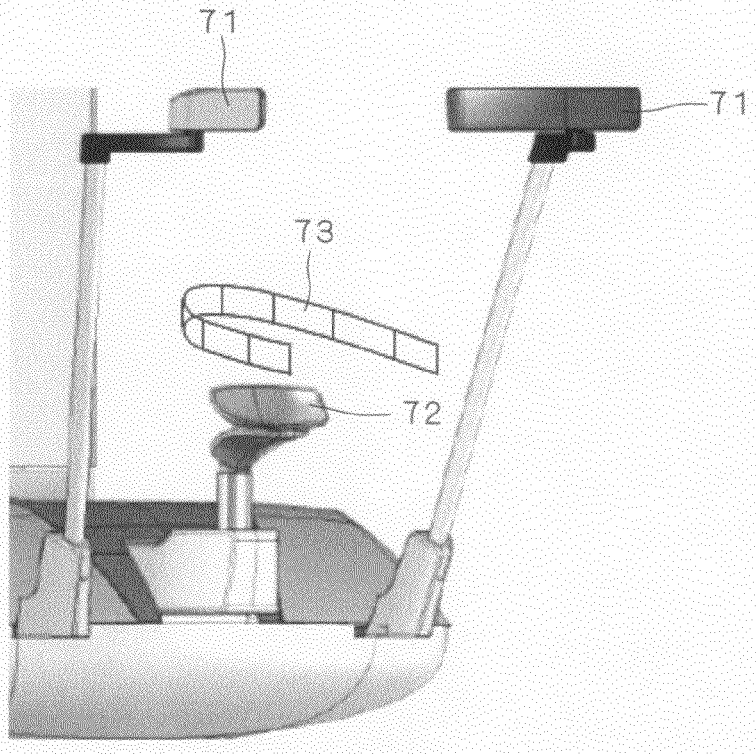

Next, an example is explained in which the position and shape of the dental arch of the object are specified from the relative positions of the head fixing unit and the X-ray computer tomography apparatus based on the information of the head fixing unit for fixing the head of the object in the X-ray computer tomography. This example deals with a case in which the X-ray computer tomography is performed by fixing the head of the object using the head fixing unit as shown in FIG. 19. The head fixing unit shown in FIG. 19 includes a head side holder 71 and a chin rest 72 as elements making up the object holding means 63 shown in FIG. 2 to fix the head sides and the chin of the object. According to this invention, however, the head fixing means is not limited to the one shown in FIG. 19, but may include a subnasal point holder or a forehead holder and the like. Also, in the X-ray imaging apparatus, the dental arch position with respect to the X-ray imaging apparatus is preset, and the object holding means 63 is arranged to hold the object in accordance with the preset dental arch position. The X-ray imaging apparatus is configured to perform the X-ray computer tomography at the position preset as the dental arch position. Alternatively, the object holding means may not be arranged in accordance with the dental arch position preset in the X-ray imaging apparatus, but the dental arch position preset in the X-ray imaging apparatus may be reset in accordance with the positional information of the object holding means. In such a case, the rotation center 3a of the rotary drive means 5 may be moved or fixed or the image data processed subsequently by the method described above with reference to the position specifying method using the positioning beams.

In this example, once the object is set in position relative to the X-ray imaging apparatus and held by the object holding means 63, etc., the position and shape of the dental arch can be estimated and specified based on the statistical data from the position of the object holding means 63 in the X-ray CT imaging apparatus shown in FIG. 2 or the relative positions of a chin rest 72 and a head side holder 71 on both sides making up the head fixture of the head fixing unit shown in FIG. 19. For example, the position of the dental arch is estimated from the position of the chin rest 72, and the shape of the dental arch is estimated by determining the size of the head from the head side holders 71 on the two sides. FIG. 19 schematically shows the estimated position and shape of the dental arch 73. In this example, the position and shape of the dental arch can be specified by the object simply fixing his/her head on the head fixing unit of the X-ray CT imaging apparatus, and therefore, the operation is very easy. Also, this apparatus can be operated in the same way as the conventional panorama X-ray imaging apparatus for dental applications, and the panorama tomogram can be easily acquired without the need of mastering the apparatus operation on the part of the operator.

Figure 20:
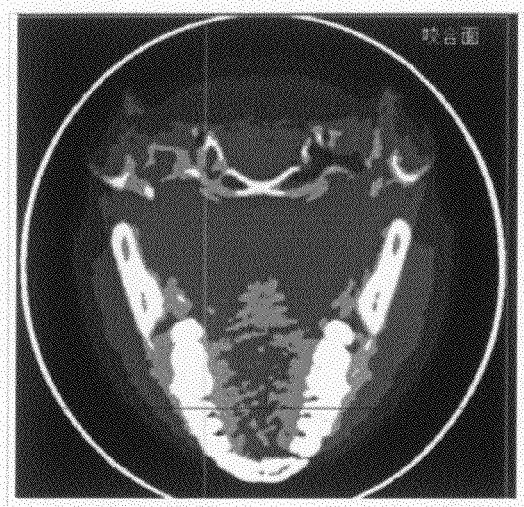

Next, an example is explained in which the X-ray projection data are subjected to the image processing in such a manner as to be binarized into the dental arch data and the other data, and the position and shape of the dental arch of the object are specified from the binarized image. The wording "binarizing the X-ray projection data" include the meaning "binarizing the three-dimensional volume data obtained by CT reconstruction of the X-ray projection data". In this example, the image (CT image) of the dental arch based on the three-dimensional volume data obtained by CT reconstruction of the X-ray projection data is subjected to the image processing for binarization in such a manner that the dental arch is colored white and the other parts black (FIG. 20). FIG. 20 shows the binarized CT image of the occlusal surface. From the contrast between the dental arch and the other parts in FIG. 20, the position and shape of the dental arch of the object are specified. In this case, the image processing method for binary display is executed by binarizing the CT image in such a manner that the dental arch and the other parts can be distinguished from each other based on a predetermined density standard according to which the dental arch, for example, is whitened.

In this example, the use of the binarized image makes it possible to specify the position and shape of the dental arch with high accuracy. Although this example represents a case in which the binarizing image processing is executed on the dental arch image based on the three-dimensional volume data obtained by CT reconstruction of the X-ray projection data, the invention is not limited to such a method, and applicable also to the binarizing image processing of the whole three-dimensional volume data obtained by CT reconstruction of the X-ray projection data or the X-ray projection data before CT reconstruction. Also, after executing the binarizing image processing on the X-ray projection data before CT reconstruction, the position and shape of the dental arch may be specified from the X-ray projection data in at least two different directions (the side image and the front image, for example) or by acquiring the three-dimensional volume data by CT reconstruction further after the binarizing image processing and taking advantage of the fact that the particular three-dimensional volume is already binarized.

Figure 21:
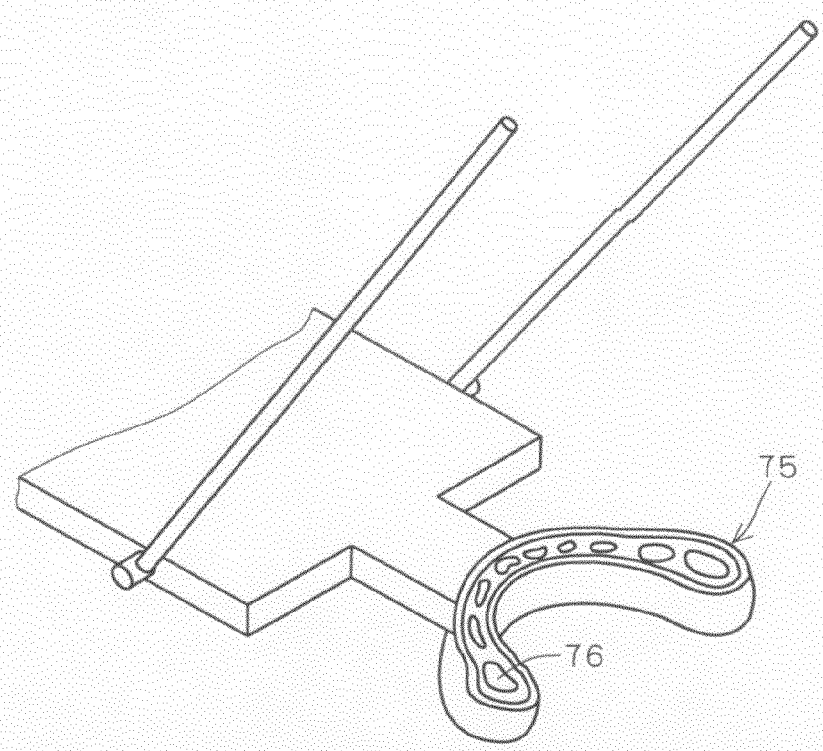

Next, an example is explained in which a dental arch identification block is mounted on the object at the time of X-ray computer tomography so that the position and shape of the dental arch of the object are specified based on the information on the dental arch identification block in the X-ray projection data. In this example, a dental arch identification block 75 in the form of mouth piece shown in FIG. 21 is bitten by the object to perform the X-ray computer tomography. The dental arch identification block 75 shown in FIG. 21 has a plurality of ceramic balls 76 buried therein, which are imaged separately from the dental arch in the X-ray projection data obtained by the X-ray computer tomography. As a result, the position and shape of the dental arch can be specified from the position and arrangement of the ceramic balls 76 displayed in the X-ray projection data. After specifying the position and shape of the dental arch on the X-ray imaging apparatus by the dental arch identification block 75, the rotation center 3*a* of the rotary drive means 5 may be moved in accordance with the position of the dental arch, or the whole head of the object may be subjected to the X-ray computer tomography without moving the rotation center 3*a* thereby to extract the dental arch projection data for the dental arch position specified in the acquired X-ray projection data on the whole head. In the latter case, since the position and shape of the dental arch can be specified on the X-ray CT imaging apparatus based on the dental arch identification block 75, the panorama tomogram can be obtained by changing only the position of the dental arch relative to the whole X-ray projection data without changing the range in which the X-ray projection data is acquired.

Also in this example, the position and shape of the dental arch can be specified accurately by the dental arch identification block 75 without the need of a special operation by the operator. Although this example deals with the dental arch identification block 75 using the ceramic balls 76, this invention may use any other materials than the ceramic balls 76 as long as the dental arch can be discriminated in the X-ray projection data.

Next, an example is explained in which the position and shape of the dental arch of the object are specified based on the X-ray transmission image taken in at least two different directions or the X-ray image with the three-dimensional volume data included in the X-ray image of the object acquired at the time of X-ray computer tomography. In this example, a simple X-ray image is taken from the front of the object and another simple X-ray image from the side of the object, from the X-ray projection data before CT reconstruction or the three-dimensional volume data acquired by CT reconstruction of the X-ray projection data. FIG. 22 shows the simple X-ray images thus retrieved. The upper diagram in FIG. 22 is the simple X-ray image taken from the side and the lower diagram in FIG. 22 the simple X-ray image taken from the front.

In this example, the position and shape of the dental arch are specified from the simple X-ray images shown in FIG. 22. Specific methods of specification include a method in which the operator sets the dental arch-specified area 81 in FIG. 22 while watching the simple X-ray images and a method in which the density pattern of the area containing the dental arch is estimated from the statistical data. Also in the present example, the use of the simple X-ray images makes it possible to specify the position and shape of the dental arch accurately. The X-ray images used in this case are not limited to the X-ray transmission images of the front and the side, but may include any image whereby the position and shape of the dental arch can be specified. Such images may include the X-ray transmission image taken from two different directions other than the front and the side and the CT image retrieved from the three-dimensional volume data in accordance with the occlusal surface of the object.

Next, an example is explained in which the position and shape are continuously designated along the dental arch in the dental arch image based on the three-dimensional volume data obtained by CT reconstruction of the X-ray projection data, and based on this designation, the position and shape of the dental arch of the object are specified. In this example, the position and shape are continuously designated along the dental arch in the dental arch image (CT image) (FIG. 23) based on the three-dimensional volume data obtained by CT reconstruction of the X-ray projection data. FIG. 23 is the CT image of the occlusal surface and shows the manner in which the position and shape of the dental arch are continuously designated along the dental arch by a designation line 80. The designation is made, for example, by tracing the dental arch with a mouse or a pen input unit on the CT image. Also in this example, the continuous designation of the position and shape along the dental arch makes it possible to specify the position and shape of the dental arch accurately.

Now, an example is explained in which the position and shape of the dental arch of the object are specified by superimposing a dental arch model image on the dental arch in the dental arch image based on the three-dimensional volume data obtained by CT reconstruction of the X-ray projection data. In this example, any one of predetermined dental arch model images 85 is superimposed on the dental arch in the dental arch image (CT image) (FIG. 24) based on the three-dimensional volume data obtained by CT reconstruction of the X-ray projection data thereby to specify the position and shape of the dental arch. FIG. 24 shows the process of superimposing, among three (A, B, C) dental arch model images 85 having different shapes, the dental arch model image 85 designated by A on the dental arch in the CT image.

Although the three types of dental arch models 85 are prepared in the case of FIG. 24, a greater number of dental arch model images 85 may be prepared if desired to specify the shape of the dental arch more accurately. Also, the dental arch model image 85 can be fitted, for example, by using a touch panel, by dragging and dropping the dental arch model image 85 with a pointer on the three-dimensional image on display, by inputting a sign of the dental arch model image 85 selected, or by inputting the coordinate.

This invention is not limited to the position specifying step and the shape specifying step according to the aforementioned specific examples in which the position and the shape of the dental arch are specified by the same process. As an alternative, the position specifying step and the shape specifying step may be different processes from each other or may share a plurality of processes to improve the accuracy of the position and shape specifying operation. For example, the CT image may be binarized as explained in this embodiment by the shape specifying step using the positioning beams explained in the other examples of the first embodiment.

In addition to above embodiment, at the position specifying step and the shape specifying step, the layer thickness setting step may be added for specifying the thickness of panorama layer in the CT image by, for example, operate a level meter, inputting thickness value, designating on the image of dental arch by mouse or pen-type unit, and the like.

As described above, in the image processing method according to this embodiment, the panorama tomogram of the dental arch of the object can be easily obtained from the X-ray projection data acquired by X-ray CT computer tomograph simply by specifying the position and shape of the dental arch of the object without any special operation or with a simple operation on the part of the operator. According to this embodiment, the image processing method is explained using the flowcharts shown in FIGS. 16 and 17. Nevertheless, the invention is not limited to this method, but a program may be employed for causing the computer to operate as a means for executing the image processing method shown in the flowcharts of FIGS. 16 and 17. Also, this invention may use a recording medium (such as a program stored in a hard disk) for storing the program. Further, the computer-readable storage medium for storing the program may be a CD-ROM or MO other than the hard disk.

While the invention has been shown and described in detail, the foregoing description is in all aspects illustrative and not restrictive. It is therefore understood that numerous modifications and variations can be devised without departing from the scope of the invention.

What is claimed is:

1. An image processing and displaying method for producing a panorama tomogram of a dentition using X-ray projection data on a dentomaxillofacial region obtained by X-ray computer tomography of a single CT scan of said dentomaxillofacial region, comprising the steps of:
    extracting dental arch projection data corresponding to a dental arch from said X-ray projection data based on preset information on a position and shape for specifying the position and shape of said dental arch in said X-ray projection data;
    generating said panorama tomogram by executing a process using said dental arch projection data; and
    displaying a panorama tomogram and a CT image selectively or simultaneously.

2. The image processing and displaying method of claim 1, wherein said panorama tomogram generating step generates said panorama tomogram by connecting a plurality of strips of image extracted from a plurality of said X-ray projection data.

3. The image processing and displaying method of claim 1, wherein said panorama tomogram generating step generates said panorama tomogram by using a portion extracted from a three-dimensional volume data obtained by CT reconstruction of said X-ray projection data.

4. The image processing and displaying method according to any one of claims 1, 2 and 3, further comprising the steps of:
    specifying a position of a dental arch of an object in said X-ray projection data; and wherein
    the preset information on the position of said dental arch in said X-ray projection data is obtained in said position specifying step.

5. The image processing and displaying method according to claim 4, wherein
    said dental arch projection data extraction step includes the step of extracting said dental arch projection data corresponding to said dental arch from said X-ray projection data by reference to the information on at least one of the X-ray incidence angle to the dentition and the thickness of a layer.

6. The image processing and displaying method according to claim 4, wherein
    said position specifying step includes the step of specifying the position of said dental arch of said object from the distance information between said object or the imaging aid mounted on said object and the X-ray computer tomography apparatus at the time of said X-ray computer tomography.

7. The image processing and displaying method according to claim 4, wherein
    said position specifying step includes the step of radiating a positioning beam on said object at the time of said X-ray computer tomography and specifying the position of said dental arch of said object from the positional information of said beam.

8. The image processing and displaying method according to claim 4, wherein
    said position specifying step includes the step of displaying a dentition image based on the three-dimensional volume data obtained by the CT reconstruction of said X-ray projection data and specifying the position of said dental arch of said object based on the input designating one reference point in said dentition image.

9. The image processing and displaying method according to any one of claims 1, 2 and 3, further comprising the steps of:
specifying a position of a dental arch of an object in said X-ray projection data; and
specifying a shape of the dental arch of the object in said X-ray projection data; and wherein
the preset information on the position and the shape of said dental arch in said X-ray projection data is obtained in said position specifying step and said shape specifying step.

10. The image processing and displaying method according to claim 9, wherein
said position specifying step and said shape specifying step include the step of displaying a dentition image based on the three-dimensional volume data obtained by CT reconstruction of said X-ray projection data and specifying the position and the shape of said dental arch of said object based on the input designating a plurality of reference points in said dentition image.

11. The image processing and displaying method according to claim 9, wherein
said position specifying step and said shape specifying step include the step of specifying the position and the shape of said dental arch of said object from the relative positions of the head fixing unit and the X-ray computer tomography apparatus based on the information on said head fixing unit for fixing the head of said object at the time of said X-ray computer tomography.

12. The image processing and displaying method according to claim 9, wherein
said position specifying step and said shape specifying step include the step of processing the image of said X-ray projection data in such a manner as to binarize said X-ray projection data into the dentition data and the other data thereby to specify the position and the shape of said dental arch of said object from said binarized image data.

13. The image processing and displaying method according to claim 9, wherein
said position specifying step and said shape specifying step include the step of mounting a dental arch identification block on said object at the time of said X-ray computer tomography and specifying the position and the shape of said dental arch of said object based on the information of said dental arch identification block in said X-ray projection data.

14. The image processing and displaying method according to claim 9, wherein
said position specifying step and said shape specifying step include the step of specifying the position and the shape of said dental arch of said object based on that X-ray transmitted image or the X-ray image of said object with the three-dimensional volume data obtained from at least two different directions at the time of said X-ray computer tomography.

15. The image processing and displaying method according to claim 9, wherein
said position specifying step and said shape specifying step include the step of displaying a dentition image based on the three-dimensional volume data obtained by CT reconstruction of said X-ray projection data and specifying the position and the shape of said dental arch of said object based on the input continuously designating the position and the shape along said dentition image.

16. The image processing and displaying method according to claim 9, wherein
said position specifying step and said shape specifying step include the step of displaying a dentition image based on the three-dimensional volume data obtained by CT reconstruction of said X-ray projection data and receiving the input of said dentition image in superposition with a dental arch model image thereby to specify the position and the shape of said dental arch of said object.

17. The image processing and displaying method according to claim 1, 2 or 3, including the steps of extracting the dental arch projection data corresponding to said dental arch from said X-ray projection data based on the preset dental arch position and shape information in said X-ray projection data to specify the position and the shape of said dental arch, and generating a panorama tomogram by executing a predetermined process using said dental arch projection data.

18. The image processing and displaying method according to claim 1, wherein said preset information on said position and shape is set prior to scanning.

19. A non-transitory computer readable medium encoded with an image processing and displaying program for causing a computer to execute processing steps of an image processing method for producing a panorama tomogram of a dentition produced by an image processing method using X-ray projection data on a dentomaxillofacial region obtained by X-ray computer tomography of a single CT scan of said dentomaxillofacial region including the steps of extracting dental arch projection data corresponding to said dental arch from the X-ray projection data based on preset position and shape information to specify a position and a shape of said dental arch in said X-ray projection data and generating said panorama tomogram by executing a predetermined process using said dental arch projection data and displaying a panorama tomogram and a CT image selectively or simultaneously.

20. An image processing and displaying apparatus comprising:
a means for storing X-ray projection data on a dentomaxillofacial region obtained by X-ray computer tomography of a single CT scan of said dentomaxillofacial region;
a means for extracting dental arch projection data corresponding to a dental arch from said X-ray projection data based on a preset position and shape information to specify a position and shape of said dental arch in said X-ray projection data;
a means for generating said panorama tomogram by executing a process using said dental arch projection data; and
displaying a panorama tomogram and a CT image selectively or simultaneously.

21. The image processing and displaying apparatus according to claim 20, further comprising:
a means for specifying a position of the dental arch of an object in said X-ray projection data; wherein
the preset positional information of said dental arch in said X-ray projection data is obtained by said position specifying means; and
said position specifying means specifies the position of said dental arch by the position specifying step included in the image processing method for producing said panorama tomogram of the dentition using said X-ray projection data on the dentomaxillofacial region obtained by the X-ray computer tomography including the steps of specifying the position of the dental arch of the object in the X-ray projection data, extracting the dental arch projection data corresponding to said dental arch from said X-ray projection data based on the positional information of said dental arch in said X-ray projection data obtained by said position specifying step, and generating said panorama tomogram by executing a process using said dental arch projection data.

22. The image processing and displaying apparatus according to claim 20, further comprising:
- a means for specifying a position of a dental arch of an object in said X-ray projection data;
- a means for specifying a shape of the dental arch of said object in said X-ray projection data; wherein
- the preset position information and shape information in said X-ray projection data is obtained by said position specifying means and said shape specifying means, respectively; and
- said position specifying means and said shape specifying means specify the position and the shape of said dental arch by the position specifying step and the shape specifying step, respectively, included in the image processing method for producing said panorama tomogram of the dentition using said X-ray projection data on the dentomaxillofacial region obtained by the X-ray computer tomography including the steps of specifying the position of the dental arch of the object in the X-ray projection data, specifying the shape of the dental arch of the object in said X-ray projection data, extracting the dental arch projection data corresponding to said dental arch from said X-ray projection data based on the position information and the shape information of the dental arch in said X-ray projection data obtained by said position specifying step and said shape specifying step, and generating said panorama tomogram by executing a process using said dental arch projection data extracted.

23. An X-ray imaging apparatus comprising an image processing and displaying apparatus including:
- an X-ray source for generating an X-ray;
- an X-ray image sensor for detecting the X-ray passed through an object;
- a means for supporting said X-ray source and said X-ray image sensor in opposed relation to each other with a head of said object there between;
- a means for rotary driving said supporting means at a time of X-ray computer tomography; and
- said image processing and displaying apparatus further including a means for storing X-ray projection data on a dentomaxillofacial region obtained by X-ray computer tomography of a single CT scan of said dentomaxillofacial region, a means for extracting dental arch projection data corresponding to said dental arch from said X-ray projection data based on a preset position and shape information to specify the position and the shape, respectively, of the dental arch in said X-ray projection data, a means for generating said panorama tomogram by executing a process using said dental arch projection data, and displaying a panorama tomogram and a CT image selectively or simultaneously.

* * * * *